United States Patent [19]

Schlom et al.

[11] Patent Number: 5,512,443
[45] Date of Patent: Apr. 30, 1996

[54] SECOND GENERATION MONOCLONAL ANTIBODIES HAVING BINDING SPECIFICITY TO TAG-72 AND HUMAN CARCINOMAS AND METHODS FOR EMPLOYING THE SAME

[75] Inventors: Jeffrey Schlom; David Colcher, both of Potomac, Md.

[73] Assignee: The United States of America as represented by the Department of Health and Human Services, Washington, D.C.

[21] Appl. No.: 547,336

[22] Filed: Jul. 2, 1990

Related U.S. Application Data

[63] Continuation of Ser. No. 73,685, Jul. 15, 1987, abandoned.
[51] Int. Cl.$^6$ .......................... G01N 33/574; G01N 33/53
[52] U.S. Cl. .......................... 435/7.23; 435/7.2; 435/7.1; 435/7.21; 435/7.9; 435/172.2; 435/240.27; 436/548; 436/63; 436/64; 436/813; 530/388.8; 530/388.85; 530/387.7; 424/9.341; 424/141.1; 424/156.1; 424/178.1; 424/174.1; 424/1.49
[58] Field of Search .......................... 435/7.2, 7.1, 7.21, 435/7.23, 7.9, 172.2, 188, 240.27, 965; 436/501, 503, 504, 517, 548, 63, 64, 512, 813; 530/387, 388.8, 388.85, 387.7; 424/141.1, 9, 156.1, 174.1, 178.1

[56] References Cited

U.S. PATENT DOCUMENTS

| | | | |
|---|---|---|---|
| 4,361,544 | 11/1982 | Goldenberg | 424/1 |
| 4,522,918 | 6/1985 | Schlom et al. | 435/68 |
| 4,565,687 | 1/1986 | Khazaeli et al. | 424/1.1 |
| 4,612,282 | 9/1986 | Schlom et al. | 435/68 |

OTHER PUBLICATIONS

Harris, W. J., "Therapeutic antibodies—the coming of age," TIBTECH, vol. 11, pp. 42–44, Feb. 1993.
Schlom, J., et al., *Cancer Res.*, vol. 52, 1067–1072, Mar. 1, 1992.
Waldmann, T. A., *Science*, vol. 252, pp. 1657–1662, 21 Jun. 1991.
Schlom et al, Cancer Res. (Suppl.). 50:820–827, 1990.
Muraro et al, Cancer Res. 48:4588–4596, 1988.
Thor et al, Cancer Res. 46:3118–3124, 1986.
Molinolo et al. Cancer Res. 50:1291–98, 1990.
Weinstein et al, 1986 on Site Specific Drug Delivery. 81–91.
Weinstein et al, 1987. Ann. N. Y. Acad. Sci. 507:199–210.
Fujimori et al. Cancer Res. 49:5656–5663, 1989.
Larson et al. Protocol, Phase I Evaluation of . . . Total of 35 Pages.
Johnson, V. G. et al, Cancer Res., vol. 46, 850–857, (Feb., 1986).
Lundy, J. et al, Cancer, vol. 57, 503–509, (1986).
Levy, R. et al, "Tumor Therapy with Monoclonal Antibodies" in *Monoclonal Antibodies in Approaches to Tumor Immunology*, a Minisymposium Summary. Federation Proceedings vol. 42, No. 9 pp. 2650–2659 (1982).

*Primary Examiner*—Toni R. Scheiner

[57] ABSTRACT

The present invention relates to second generation monoclonal antibodies having binding specificity to a tumor associated glycoprotein having an approximate molecular weight of >10$^6$d ("TAG-72") and human carcinomas and methods for employing the same. Hybridomas producing such antibodies have been prepared.

44 Claims, 5 Drawing Sheets

COMPETITION vs
125-I B72.3 IgG

SPRIA vs BREAST CA AND
COLON CA EXTRACT

COMPETITION vs
125-I B72.3 IgG

SPRIA vs BREAST CA AND
COLON CA EXTRACT

Ab DILUTION (1 : 5)

Ab DILUTION (1 : 5)

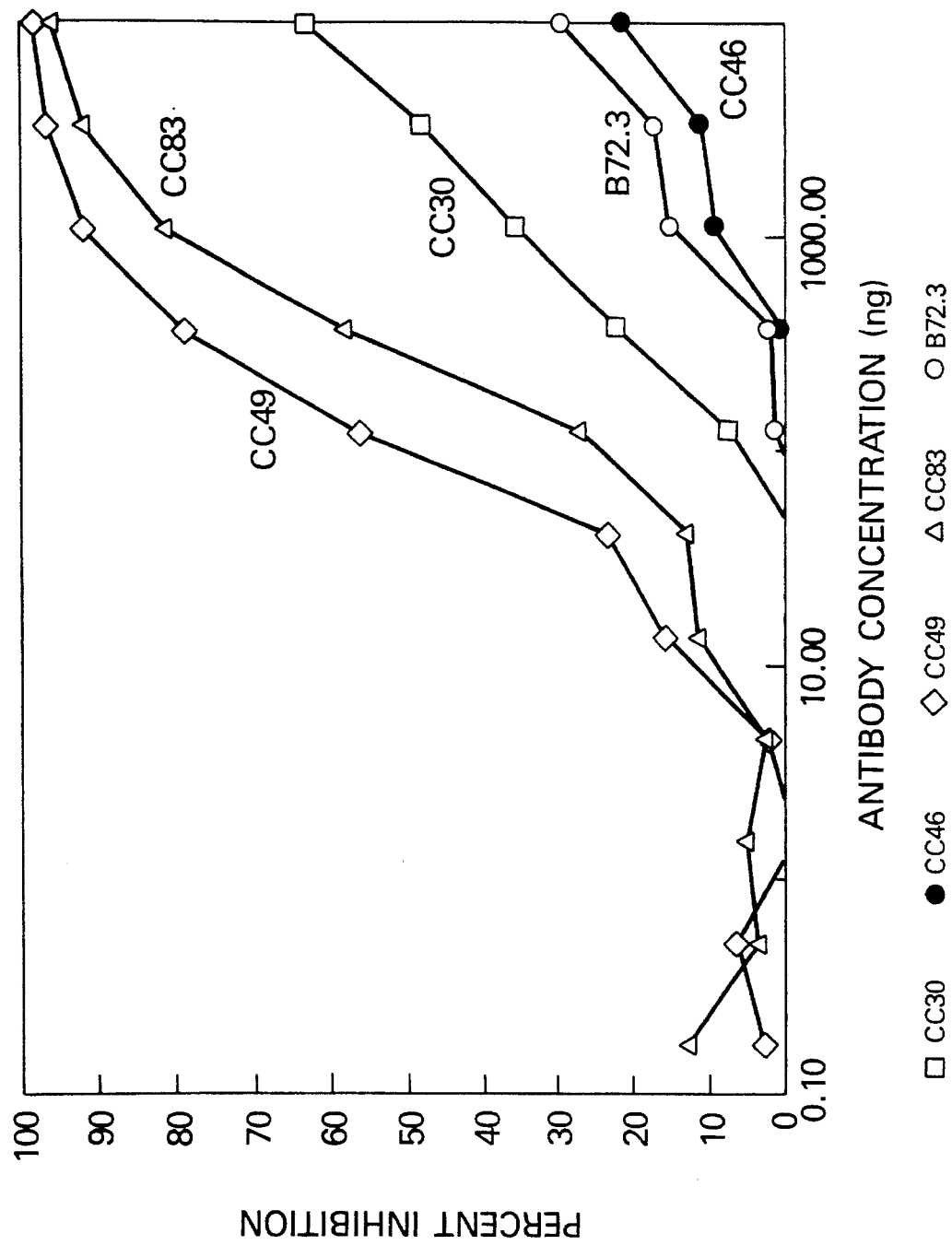

□ blood  ● liver  ◆ spleen  △ kidney  ○ lung

SECOND GENERATION MONOCLONAL ANTIBODIES HAVING BINDING SPECIFICITY TO TAG-72 AND HUMAN CARCINOMAS AND METHODS FOR EMPLOYING THE SAME

FIELD OF THE INVENTION

This application is a continuation of U.S. Ser. No. 07/073,685, filed Jul. 15, 1987 and now abandoned.

The present invention relates to second generation monoclonal antibodies having binding specificity to a tumor associated glycoprotein having an approximate molecular weight of $>10^6$d (hereinafter "TAG-72") and human carcinomas, and methods for employing the same.

BACKGROUND OF THE INVENTION

Numerous monoclonal antibodies have been developed which have binding specificity for a variety of human carcinomas (see Schlom, J. et al, *Important Advances in Oncology*, Philadelphia, Pa., J.B. Lippincott Co., Vol. 1, pp. 170–192 (1984) and Schlom, J., *Cancer Res.*, 46: 3225–3238 (1986). One of these monoclonal antibodies designated B72.3 (see Colcher, D. et al, *Proc. Natl. Acad. Sci. USA.* 78: 3199–3203 (1981) and U.S. Pat. Nos. 4,522,918 and 4,612,282), is a murine $IgG_1$, and was developed using a human breast carcinoma extract as the immunogen. Monoclonal antibody B72.3 is produced by hybridoma B72.3 (ATCC No. HB-8108) and has been extensively studied. Monoclonal antibody B72.3 has been shown to be distinct from other known monoclonal antibodies on the basis of: (1) its binding specificity to TAG-72 (see Johnson, V. G. et al, *Cancer Res.*, 46: 859–857 (1986)); (2) its binding specificity to various types of human carcinoma tissues, including breast, ovarian, lung, colorectal, endometrial and pancreatic carcinoma tissues (see Nuti, M. et al, *Intl. J. Cancer*, 29: 539–545 (1982); Stramignoni, D. et al, *Intl. J. Cancer*, 31: 543–552 (1983), Thor, A. et al, *J. Natl. Cancer Inst.* 76: 995–1006 (1986); and Thor, A. et al, *Cancer Res.*, 46: 3118–3124 (1986)); (3) its lack of binding specificity to normal adult human tissues (see Nuti, M. et al, *Intl. J. Cancer*, 29: 539–545 (1982); Stramignoni, D. et al, *Intl. J. Cancer*, 31: 543–552 (1983); Thor, A. et al, *J. Natl. Cancer Inst.*, 76: 995–1006 (1986); and Thor, A. et al, *Cancer Res.*, 46: 3118–3124 (1986)); (4) its ability to detect TAG-72 in serum (see Paterson, A. J. et al, *Int. J. Cancer*, 37: 659–666 (1986) and Klug, T. L. et al, *Int. J. Cancer*, 38: 661–669 (1986)); (5) its ability to detect carcinoma cells in human effusions and fine needle aspiration biopsies (see Szpak, C. A. et al, *Acta Cytologica*, 28: 356–367 (1984); Johnston, W. W. et al, *Cancer Res.*, 45: 1894–1900 (1986); Szpak, C. A. et al, *Am. J. Path.*, 122: 252–260 (1986); Johnston, W. W. et al, *Human Path.*, 17: 501–513 (1986); Martin, S. E. et al, *Am. J. Clin. Path*, 86: 10–18 (1986); Nuti, M. et al, *Int. J. Cancer*, 37: 493–498 (1986) and Johnston, W. W. et al, *Cancer Res.*, 46: 6462–6470 (1986)); and (6) its binding specificity and prolonged binding to human carcinomas both in experimental animal systems (see Keenan, A. M. et al, *J. Nucl. Med.*, 25: 1197–1203 (1984) and Colcher, D. et al, *Cancer Res.*, 44: 5744–5751 (1984)) and in clinical trials (see Colcher, D. et al, *Cancer Res.*, 47: 1185–1189 (1987) and Esteban, J. M. et al, *Int. J. Cancer*, 39: 50–58 1987)).

However, monoclonal antibody B72.3 is disadvantageous in that (1) B72.3 does not have binding specificity to every human carcinoma tissue of a particular type, e.g., to every ovarian, colon carcinoma tissue, etc. (see Nuti, M. et al, *Intl. J. Cancer*, 29: 539–545 (1982); Stramignoni, D. et al, *Intl. J. Cancer*, 31: 543–552 (1983); Thor, A. et al, *J. Natl. Cancer Inst.*, 76: 995–1006 (1986); Thor, A. et al, *Cancer Res.*, 46: 3118–3124 (1986) and Horan Hand, P. et al, *Cancer Res.*, 42: 728–735 (1983)); (2) B72.3 does not have binding specificity to all carcinoma cells within a given human carcinoma mass (see Nuti, M. et al, *Intl. J. Cancer*, 29: 539–545 (1982); Stramignoni, D. et al, *Intl. J. Cancer*, 31: 543–552 (1983); Thor, A. et al, *J. Natl. Cancer Inst.*, 76: 995–1006 (1986); Thor, A. et al, *Cancer Res.*, 46: 3118–3124 (1986) and Horan Hand, P. et al, *Cancer Res.*, 43: 728–735 (1983)); (3) B72.3 does not have binding specificity to most human carcinoma cell lines in culture (see Horan Hand, P. et al, *Cancer Res.*, 43: 728–735 (1983); Horan Hand, P. et al, *Cancer Res.*, 45: 833–840 (1985) and Friedman, E. et al, *Cancer Res.*, 45: 5648–5655 (1985)); (4) it is difficult to obtain highly immunoreactive $F(ab')_2$, $F(ab')$ and Fab fragments from B72.3, such fragments being necessary for efficient in vivo immunodiagnostic and therapeutic applications; and (5) since B72.3 is of the $IgG_1$ isotype, it is difficult to conduct monoclonal antibody effector cell mediated cytotoxicity or complement mediated cytotoxicity studies using B72.3 ($IgG_{2a}$, $IgG_{2b}$ or IgM isotypes being more efficient for these applications).

SUMMARY OF THE INVENTION

Accordingly, an object of the present invention is to provide monoclonal antibodies which have binding specificity to a variety of human carcinomas, including human carcinomas of a given type for which B72.3 essentially has no binding specificity.

Another object of the present invention is to provide monoclonal antibodies having high binding affinity for TAG-72 and human carcinomas.

A further object of the present invention is to provide monoclonal antibodies from which highly immunoreactive $F(ab')_2$, $F(ab')$ and Fab fragments can be easily obtained for use in in vivo immunodiagnosis and therapy of human carcinomas.

A still further object of the present invention is to provide monoclonal antibodies from which recombinant antibodies can be obtained for use in in vivo immunodiagnosis and therapy of human carcinomas.

An additional object of the present invention is to provide monoclonal antibodies of the $IgG_{2a}$, $IgG_{2b}$ and IgM isotypes which have binding specificity for human carcinomas for use in conducting monoclonal antibody effector cell mediated cytotoxicity or complement mediated cytotoxicity studies.

Still an additional object of the present invention is to provide methods for diagnosing in vitro and in vivo human carcinomas and methods for treating human carcinomas employing these monoclonal antibodies.

Other objects and advantages of the present invention will become apparent from the Detailed Description of the Invention presented hereunder.

The above and various other objects and advantages of the present invention are achieved by the second generation monoclonal antibodies of the present invention which have binding affinity to both TAG-72 and to LS174T antigen(s).

Unless defined otherwise all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

As used herein, the expression "second generation monoclonal antibodies" means monoclonal antibodies produced using, as the immunogen, an antigen which has been affinity purified with a first generation monoclonal antibody. As used herein, the expression "first generation monoclonal antibody" means a monoclonal antibody produced using, as the immunogen, a crude cell extract.

The term "substantially" as used herein means almost wholly or to a large extent, but not entirely.

LS174T (ATCC No. CL 188) is a variant of the LS180 (ATCC No. CL 187) colon adenocarcinoma line. It is more easily subcultivated than the parent line. It is tumorigenic in nude mice. The karyotype is similar to that of LS180 with a missing X chromosome in a majority of the cells. Electron microscopic studies reveal abundant microvilli and intracytoplasmic mucin vacuoles (see Tom, B. H. at el, In Vitro 12: 180–191 (1976)).

TAG-72 is an antigen found in the LS174T tumor cell line. Monoclonal antibody B72.3 binds to a high molecular weight tumor associated glycoprotein identified as TAG-72. Data has been presented as described in Johnson, V. G. et al, *Cancer Res.*, 46: 850–857 (1986), to characterize the TAG-72 molecule as a mucin. This conclusion is based on the following observations: (a) TAG-72 has a high molecular weight ($>1\times10^6$) as shown by its exclusion from a Sepharose CL-4B column; (b) the density of TAG-72 determined by equilibrium centrifugation in CsCl was 1.45 gm/ml, indicating a heavily glycosylated glycoprotein; (c) TAG-72 demonstrates a change in migration after neuraminidase digestion, indicating that it is a heavily sialylated molecule with an abundance of O-glycosidically linked oligosaccharides characteristic of mucins; (d) blood group antigens commonly found on mucins are found on affinity-purified TAG-72; and (e) Chondroitinase ABC digestion had no effect on TAG-72, thus demonstrating that the TAG-72 epitope is not expressed on a chondroitin sulfate proteoglycan.

More specifically, the above-described objects of the present invention have been achieved by the second generation monoclonal antibodies of the present invention, immunoreactive fragments or recombinants thereof which have binding specificity to TAG-72 and to human carcinomas, including human carcinomas to which antibody B72.3 has minimal binding specificity and with minimal binding specificity to normal adult human tissues. The term "minimal" means the least possible or substantially inconsequential.

In another embodiment, the above-described objects of the present invention have been achieved by a method for diagnosing a human carcinoma or metastases thereof comprising:

(a) obtaining a body sample, such as body fluid, tissue or biopsy from a patient;

(b) contacting the body sample material with a second generation monoclonal antibody of the present invention, an immunoreactive fragment or a recombinant thereof;

(c) determining the level of binding of second generation monoclonal antibody, immunoreactive fragment or recombinant thereof to the body sample material; and (d) comparing the amount of second generation monoclonal antibody, immunoreactive fragment or recombinant thereof bound to substances present in the body sample to a control sample or to a predetermined base level, so that a binding greater than the control level is indicative of the presence of human carcinomas or metastases thereof.

In still another embodiment, the above-described objects of the present invention have been achieved by a method for diagnosing the presence of a human carcinoma or metastases thereof comprising:

(a) administering to a patient a second generation monoclonal antibody of the present invention, an immunoreactive fragment or recombinant thereof, conjugated to an imaging marker; and (b) exposing the patient to a means for detecting said imaging marker to identify areas of imaging marker corresponding to a human carcinoma or metastatic sites thereof in said patient.

In a still further embodiment, the above-described objects of the present invention have been achieved by a method of treating a patient afflicted with a human carcinoma or metastases thereof, comprising administering to a patient afflicted with carcinoma or metastases a pharmaceutically effective amount of a second generation monoclonal antibody of the present invention, an immunoreactive fragment or recombinant thereof conjugated to a therapeutic agent.

BRIEF DESCRIPTION OF THE DRAWINGS

FIG. 3 is an analysis of a competition RIA with CC49, wherein $^{125}$I-labeled CC49 monoclonal antibody was reacted with LS-174T colon carcinoma cell extract and purified CC30, CC46, CC49, CC83 and B72.3 were used as competing antibodies.

DETAILED DESCRIPTION OF THE INVENTION

I. Characteristics of the Monoclonal Antibodies

Figure 1:
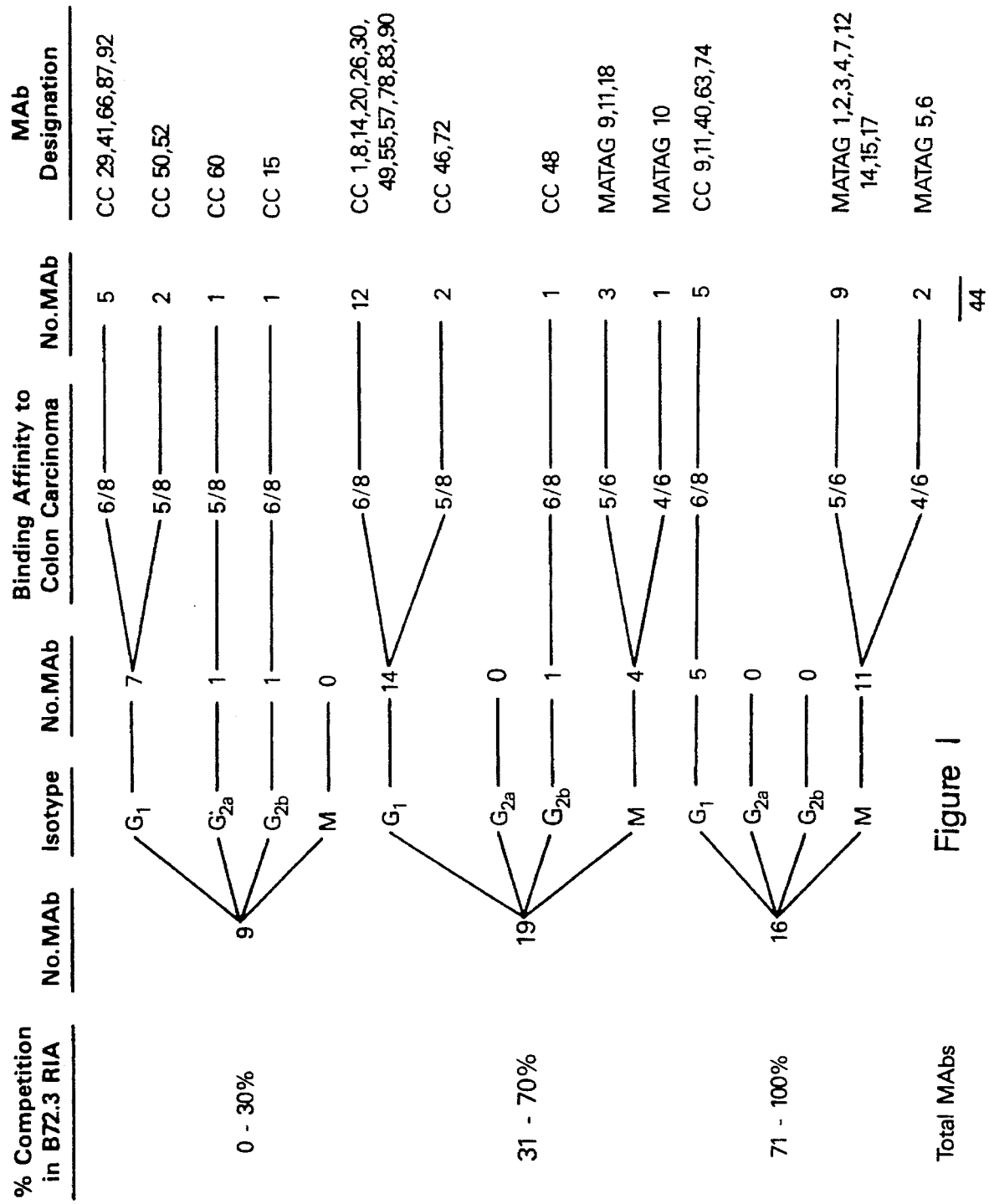
FIG. 1 is a schematic diagram of: (1) the differential binding specificities of the CC and MATAG monoclonal antibodies of the present invention to LS-174T colon carcinoma cells (ATCC No. CRL-188) in a competition radioimmunoassay (hereinafter "RIA") with B72.3; (2) the isotypes of the CC and MATAG monoclonal antibodies of the present invention; and (3) the binding specificity of the CC and MATAG monoclonal antibodies of the present invention to various colon carcinomas in a solid phase RIA (hereinafter "SPRIA").

The monoclonal antibodies specifically developed in the present invention, designated CC 1 to CC 92 (IgG monoclonal antibodies) and MATAG 1 to MATAG 18 (IgM monoclonal antibodies) (see FIG. 1) all have binding specificity to TAG-72 and numerous types of human carcinomas (including breast, ovarian, lung, colorectal, endometrial and pancreatic carcinomas), and are different from B72.3 in that they:

(1) have binding specificity to more human carcinomas than B72.3 while still maintaining essentially no specificity to normal adult human tissues;

(2) have a higher binding affinity for TAG-72 than B72.3 i.e., on the order of greater than $3 \times 10^9$M, preferably greater than $8 \times 10^9$M and consequently bind human carcinomas in vivo at a higher efficiency;

(3) exhibit a 50% or more efficiency than B72.3 in targeting human carcinomas in-situ (i.e., 50% more injected dose/gram tumor than B72.3 and preferably greater than 100% more injected dose/gram tumor than B72.3);

(4) can be easily fragmented with pepsin to obtain F(ab')$_2$, F(ab') and Fab fragments that are highly immunoreactive; and (5) include monoclonal antibodies of the IgG$_{2a}$, IgG$_{2b}$, and IgM isotypes so they can more efficiently be used in monoclonal antibody targeted effector cell mediated cytotoxicity or complement mediated cytotoxicity studies.

The development of the CC and MATAG monoclonal antibodies of the present invention also now makes feasible the use of double determinant RIAs (hereinafter "DDRIA"s) for more efficient detection of human carcinoma antigens in body fluids and biopsies of cancer patients.

II. Production of the Monoclonal Antibodies

The CC and MATAG monoclonal antibodies of the present invention are produced by immunizing mice (or other animals such as rats, rabbits, goats, and humans) with purified TAG-72 obtained from various xenografts, such as LS-174T human colon carcinoma xenografts prepared using LS-174T carcinoma cells (ATCC No. CRL-188) and OVCAR-3 human ovarian cancer xenografts, prepared using OVCAR-3 carcinoma cells (see Hamilton, T. C. et al, *Cancer Res.*, 43: 5379–5389 (1983)).

TAG-72 is purified from the xenografts by methods well known in the art. More specifically, by the following steps (1) breaking the cells (2) centrifuging and/or filtering to remove cellular debris, (3) carrying out sizing column chromatography to obtain proteins having a molecular weight of >10$^6$d, i.e., the molecular weight of TAG-72, and then (4) carrying out B72.3 affinity column chromatography to obtain the desired TAG-72 (see Paterson, A. J. et al, *Intl. J. Cancer,* 37: 659–666 (1986)).

Immunizing the animals, e.g. mice, with the purified TAG-72, isolating the immunized cells, fusing the immunized cells with mouse myeloma cells (or myeloma cells of other species such as rats, rabbits, goats and humans), all of which are well known in the art and readily available, and culturing the resulting fused cells under conditions which allow for growth of hybridomas, are all conducted by methods well known or readily determined in the art (see Herzenberg, L. A. et al., *Handbook of Experimental Immunology,* Oxford, Blackwell pp. 25.1–25.7; Colcher, D. et al, *Proc. Natl. Acad. Sci. (USA),* 78: 3199–3203 (1981); and Muraro, R. et al., *Intl. J. Cancer,* 39: 34–44 (1987)).

The resulting hybridomas are then tested to isolate those which produce monoclonal antibodies having binding specificity to TAG-72 and human carcinomas but not to normal adult human tissues. This screening is carried out using a SPRIA as described in greater detail in the Examples provided hereinafter.

The binding affinity of monoclonal antibodies for TAG-72 is determined by means well known in the art (see Heyman, B. et al, *J. Immunol. Methods,* 68: 193–204 (1984) and as described in detail in the Examples provided hereinafter.

The isotypes (IgG$_1$, IgG$_{2a}$, IgG$_{2b}$, IgG$_3$ or IgM) of the monoclonal antibodies are determined by means well known in the art (see Colcher, D. et al, *Cancer Res.* 41: 1451–1459 (1981)) and as described in detail in the Examples provided hereinafter.

In the non-limiting Examples provided hereinafter, in excess of four thousand hybridomas were produced by fusing (i) spleen cells of mice immunized with purified TAG-72 which was obtained from a LS-174T human colon carcinoma xenograft, and (ii) the well known and readily available NS-1 mouse myeloma line (ATCC No. TIB-18). From these hybridomas, 44 double cloned hybridomas (29 CC second generation monoclonal antibodies and 15 MATAG second generation monoclonal antibodies) were selected and characterized as described in the Examples provided hereinafter.

The CC monoclonal antibodies of the present invention are fragmented to obtain highly immunoreactive F(ab')$_2$, F(ab') and Fab fragments using the enzyme pepsin by methods well known in the art (see Colcher, D. et al., *Cancer Res.,* 43: 736–742 (1983)) and as described in greater detail in the Examples provided hereinafter. The immunoreactivity of the resulting F(ab')$_2$, F(ab') and Fab fragments are determined in a competition RIA or SPRIA as described above for the complete monoclonal antibody molecule.

The second generation antibodies of the present invention are also made into recombinant forms by techniques of molecular biology well known in the art (see Rice, D. et al, *Proc. Natl. Acad. Sci., USA,* 79: 7862–7865 (1982); Kurokawa, T. et al, *Nucleic Acids Res.,* 11: 3077–3085 (1983); Oi, V. T. et al, *Proc. Natl. Acad. Sci., USA,* 80: 825–829 (1983); Boss, M. A. et al, *Nucleic Acids Res.* 12: 3791–3806 (1984); Boulianne, G. L. et al, *Nature (London)* 312: 643–646 (1984); Cabily, S. et al, *Proc. Natl. Acad. Sci., USA,* 81: 3273–3277 (1984); Kenten, J. et al, *Proc. Natl. Acad. Sci., USA,* 81: 2955–2959 (1984); Liu, F-T, et al, *Proc. Natl. Acad. Sci., USA,* 81: 5369–5373 (1984); Morrison, S. L. et al, *Proc. Natl. Acad. Sci., USA,* 81: 6851–6855 (1984); Neuberger, M. S. et al, *Nature (London),* 312: 604–608 (1984); Potter, H. et al, *Proc. Natl. Acad. Sci., USA,* 81: 7161–7165 (1984); Neuberger, M. S. et al, *Nature (London)* 314: 268–270 (1985); Jones, P. T. et al, *Nature (London),* 321: 522–525 (1986); Oi, V. T. et al, *BioTechniques,* 4: 214–221 (1986); Sahagan, B. G. et al, *J. Immunol.,* 137: 1066–1074 (1986); Sun, L. K. et al, *Hybridoma* 5 (*Suppl.* 1):

S17– S20 (1986); and Sun, L. K. et al, *Proc. Natl. Acad. Sci, USA,* 84: 214–218 (1987)) all of which are specifically incorporated herein by reference.

More specifically, the second generation monoclonal antibodies of the present invention are altered to a chimeric form by substituting, e.g., human constant regions ($F_c$ domains) for mouse constant regions by recombinant DNA techniques known in the art as described in the above cited references. These $F_c$ domains can be of various human isotypes, i.e., $IgG_1$, $IgG_2$, $IgG_3$ $IgG_4$ or IgM.

In addition, the second generation monoclonal antibodies of the present invention are altered to an affinity modified form, avidity modified form, or both, by altering binding sites or altering the hinge region using recombinant DNA techniques well known in the art as described in the above cited references.

The recombinant antibody forms are also fragmented to produce immunoreactive fragments F(ab')$_2$, F(ab') or F(ab) in the same manner as described above in which the second generation monoclonal antibodies of the present invention are fragmented.

Accordingly, as used herein, the expression "recombinant antibodies" collectively includes chimeric/recombinant forms of the second generation monoclonal antibody of the present invention wherein the $F_c$ domain is substituted for an $F_c$ domain of another species or isotype, affinity modified forms of the second generation monoclonal antibody of the present invention wherein the binding sites are altered, avidity modified forms of the second generation monoclonal antibody of the present invention wherein the hinge regions are altered, immunoreactive fragments thereof and combinations thereof.

The second generation monoclonal antibodies of the present invention are produced in large quantities by injecting a hybridoma producing a second generation monoclonal antibody of the present invention into the peritoneal cavity of pristane-primed mice, and after an appropriate time (about 1–2 weeks), harvesting ascites fluid from the mice, which yields a very high titer of homogenous monoclonal antibody, and isolating the monoclonal antibodies therefrom by methods well known in the art (see Stramignoni, P. et al, *Intl. J. Cancer,* 31: 543–552 (1983)). Alternatively, the second generation monoclonal antibodies are produced by culturing a hybridoma producing a second generation monoclonal antibody of the present invention in vitro and isolating secreted monoclonal antibodies from the cell culture medium by methods well known in the art (see Colcher, D. et al, *Proc. Natl. Acad. Sci., USA,* 78: 3199–3203 (1981)).

The CC and MATAG monoclonal antibodies of the present invention are thus produced according to the above method. The binding specificity and binding affinity of these monoclonal antibodies and a comparison of such with B72.3 are discussed in greater detail in the Examples provided hereinafter.

III. Uses of the Monoclonal Antibodies

The second generation monoclonal antibodies of the present invention, immunoreactive fragments or recombinants thereof, can be used either alone, in combination with one another, or in combination with other antibodies, such as B72.3 or immunoreactive fragments thereof, in: (1) in vitro diagnostic assays using labelled monoclonal antibodies for the detection of TAG-72 in body fluids of patients; (2) in vivo diagnostic assays (diagnostic imaging) using the second generation monoclonal antibodies, of the present invention, immunoreactive fragments or recombinants thereof, conjugated to an imaging marker, for the in situ detection of carcinoma lesions, (3) in vivo cancer treatment using the second generation monoclonal antibodies of the present invention, immunoreactive fragments or recombinants thereof alone or conjugated to a therapeutic agent such as a radionuclide, drug, toxin, effector cells, other antibodies or via a complement mechanism; (4) immunohistopathology or immunocytochemistry for the detection or phenotyping of carcinoma cells; and (5) as immunogens to activate the anti-idtotype network for active immunotherapy against carcinomas.

A. In Vitro Diagnostic Assays

In vitro diagnostic assays of human carcinomas or metastases thereof by detecting TAG-72 in body fluids of patients using the second generation monoclonal antibodies of the present invention, immunoreactive fragments or recombinants thereof are described in greater detail below.

The body fluid obtained from a patient is contacted with the monoclonal antibody of the present invention, immunoreactive fragment or recombinant thereof. A diagnosis is then made by determining the amount of monoclonal antibody, immunoreactive fragment or recombinant thereof binding to substances (TAG-72) present in the body fluid and comparing the amount of monoclonal antibody, immunoreactive fragments or recombinants thereof bound to the body fluid substances to a predetermined base level as hereinafter defined. The amount of bound monoclonal antibody, immunoreactive fragment or recombinant thereof exceeding the base level indicates the presence of a human carcinoma or metastases thereof.

Examples of body fluids which can be used in the in vitro method are any body fluids suspected of containing TAG-72. Preferred examples thereof include blood (serum or plasma), sputum, nipple discharge, cyst fluid, ascites fluids, pleural effusions, seminal plasma, semen, urine and, prostatic fluid and/or biopsy specimens. Serum or plasma are the more preferred body fluids employed in the present invention. The body fluids can be obtained by methods readily known to or determined by those skilled in the art.

The body fluid is contacted with the second generation monoclonal antibody of the present invention, immunoreactive fragment or recombinant thereof and the amount of monoclonal antibody, immunoreactive fragment or recombinant thereof bound to substances in the body fluid is determined by means of immunochemical assays well known to those skilled in the art, as described, for example, in Klug, T. L. et al, *Cancer Res.,* 44: 1048–1053 (1984); Klug, T. L. et al, *Int. J. Cancer,* 38: 661–669 (1986), Herlyn, M. et al, *J. Clin. Immunol.,* 2: 135–140 (1982), Metzgar, R. S. et al, *Proc. Natl. Acad. Sci., USA,* 81: 5242–5246 (1984), Papsidero, L. D. et al, *Cancer Res.,* 44: 4653–4657 (1984), Hayes, D. F. et al, *J. Clin. Invest.,* 75: 1671–1678 (1985), Killian, C. S. et al, *Cancer Res.,* 45: 886–891 (1985), Hedin, A et al, *Proc. Natl. Acad. Sci., USA,* 80: 3470–3474 (1983), Pekary, A. E. et al, *Clin. Chem.,* 30: 1213–1215 (1984), Bast, R. C. et al, *New England J. Med.,* 309: 883–887 (1983) and Bellet, D. H. et al, *Proc. Natl. Acad. Sci., USA,* 81: 3869–3873 (1984), the disclosures of all of which are specifically incorporated herein by reference.

An example of one type of immunochemical assay useful in the present invention is a sandwich immunoradiometric assay (hereinafter "IRMA"). In this type of assay, the presence of antigen (TAG-72) is measured directly by reacting it with an excess of labeled monoclonal antibody. In such an assay, before the antigen is reacted with the labeled monoclonal antibody, the antigen is insolubilized on an immunoadsorbent which specifically, binds the antigen. The immunoadsorbent is formed by affixing a second generaton monoclonal antibody, immunoreactive fragment or recombinant thereof to a substrate such as an immunobead. In sandwich assays for an antigen which is monomeric, two antibodies which recognize distinct epitopes on the antigen are required, i.e., a so-called "double determinant" assay, so that there is no competition for binding to the antigen. In sandwich asays, one antibody is bound to the immunoadsorbent and the other antibody is used as the labeled tracer. In assays for dimeric or polymeric antigens, the same antibody can be bound to the immunoadsorbent as the labeled tracer.

Sandwich IRMA's may be performed in a forward, reverse or simultaneous mode.

In a forward sandwich assay for TAG-72, a monoclonal antibody is affixed to a solid phase such as an immunobead to form an immunoadsorbent specific for TAG-72. A body liquid sample containing TAG-72 is then incubated with the immunoadsorbent. Incubation is maintained for a sufficient period of time to allow TAG-72 in the body fluid to bind to the immobilized monoclonal antibody on the immunoadsorbent. After this first incubation, the solid phase immunoadsorbent is separated from the incubation mixture. The immunoadsorbent may be washed to remove unbound interfering substances, such as non-specific binding proteins, which may also be present in the body fluid. The immunoadsorbent containing TAG-72 bound to an immobilized monoclonal antibody is subsequently incubated with a labeled monoclonal antibody, immunoreactive fragment or recombinant thereof. Again, the incubation is carried out for a period of time and under conditions sufficient to ensure binding of the labeled monoclonal antibody, immunoreactive fragment or recombinant thereof to TAG-72. After the second incubation, another wash may be performed to remove unbound labeled monoclonal antibody, immunoreactive fragment or recombinant thereof from the solid phase immunoadsorbent. The labeled monoclonal antibody, immunoreactive fragment or recombinant thereof bound to the solid phase immunoadsorbent is then measured, and the amount of labeled monoclonal antibody, immunoreactive fragment or recombinant thereof detected serves as a direct measure of the amount of TAG-72 present in the body fluid.

The sandwich IRMA may also be performed in reverse and simultaneous modes. In the reverse mode, an incubation mixture is formed of the body fluid to be tested and a soluble labeled monoclonal antibody, immunoreactive fragment or recombinant thereof directed against TAG-72. The mixture is incubated, then contacted with a solid phase immunoadsorbent also containing a monoclonal antibody, immunoreactive fragment or recombinant thereof directed against TAG-72. After another incubation, the immunoadsorbent is separated from the mixture and the label bound to the immunoadsorbent is taken as an indication of the amount of TAG-72 in the body fluid.

In the simultaneous mode, an incubation mixture is formed of the body fluid, the labeled monoclonal antibody, immunoreactive fragment or recombinant thereof and the solid phase immunoadsorbent. After incubation for sufficient time, the solid phase immunoadsorbent is separated from the mixture and the label associated with the immunoadsorbent is measured to give an indication of the amount of TAG-72 in the body fluid.

For each incubation step in the various assay modes described above, the time and conditions of incubation are selected to ensure maximum binding of TAG-72 to the immobilized monoclonal antibody, immunoreactive fragment or recombinant thereof and to labeled monoclonal antibody, immunoreactive fragment or recombinant thereof, but generally are about 6 to 16 hours at room temperature (22° to 27° C.).

In addition to the IRMA's described above, other immunoassays useful in the present invention include competitive binding assays such as RIAs and fluorescent or enzymelinked immunoassays (hereinafter "ELISA"). One suitable type of RIA is a SPRIA.

For a SPRIA, a solid phase immunoadsorbent is prepared as described for the IRMA.

The immunoadsorbent is then incubated with the body fluid and a known amount of labeled TAG-72 for a period of time and under conditions which permit binding of TAG-72 to the immunoadsorbent. The immunoadsorbent is separated from the body fluid and the amount of label associated therewith is assessed. By reference to a pre-established inhibition curve defining the relationship between labeled TAG-72 associated with the immunoadsorbent, the amount of unlabeled human TAG-72 in the body fluid is determined.

In the various SPRIAs, the immunoadsorbent is separated from incubation mixtures containing the body fluid, the labeled antibody or both. Separation can be accomplished by any conventional separation technique such as sedimentation or centrifugation. Preferably, though not necessarily, the immunoadsorbent is washed prior to contacting it, when required, with a second incubation medium and prior to measuring the amount of label associated with the immunoadsorbent. The washing removes non-specific interfering substances or excess labeled antibody which may affect the accuracy and sensitivity of the assay.

The particular label employed to label the second generation monoclonal antibodies of the present invention, immunoreactive fragments or recombinants thereof or TAG-72 in the above-described assays is not critical to the present invention and can be a radioisotope such as $^{32}P$, $^{14}C$, $^{3}H$, $^{125}I$, $^{131}I$, or $^{35}S$ for the IRMA and RIA or a fluorescent molecule such as fluorescein or rhodamine or an enzyme, which, under the presence of an appropriate substrate converts the substrate to a color product for the ELISA. Examples of such enzymes include alkaline phosphatase and horseradish peroxidase.

As the last step in the in vitro diagnostic method according to the present invention, the amount of second generation monoclonal antibody, immunoreactive fragment or recombinant thereof, binding to substances (TAG-72) present in the body fluid is compared to a predetermined base level.

The determination of the base level of monoclonal antibody assay binding to be expected is a determination routinely made by those of ordinary skill in the art when defining the parameters necessary for reading of a diagnostic test of this sort. These determinations may be made without undue experimentation, particularly in light of the teachings set forth herein.

Generally, the "base level" is defined as (1) two standard deviations above the mean of the normal population, or (2) the level below which 99% of the normal population falls.

B. In Vivo Diagnostic Assays

In vivo diagnostic assay of human carcinomas or metastases thereof using the second generation monoclonal antibodies of the present invention, immunoreactive fragments or recombinants thereof, are described in more detail below.

A second generation monoclonal antibody of the present invention, immunoreactive fragment or recombinant thereof, conjugated to an imaging marker is administered to a patient (or subsequently administering the marker or linker conjugated marker after administration of the second generation monoclonal antibody) and then the presence of the imaging marker in the patient is detected by exposing the patient to an appropriate means for detecting the marker.

Administration and detection of the antibody-imaging marker conjugate as well as methods of conjugation of the antibody to the imaging marker are accomplished by methods readily known to or readily determined by those skilled in the art, as described, for example, in Goldenberg, D. M. et al, *New England J. Med.,* 298-1384–1388 (1978); Goldenberg, D. M. et al, *J. A. M. A.,* 250: 630–635 (1983); Goldenberg, D. M. et al, *Gastroenterol.,* 84: 524–532 (1983); Siccardi, A. G. et al *Cancer Res.,* 46: 4817–4822 (1986); Epenetos, A. A. et al, *Cancer,* 55: 984–987 (1985); Philben, V. J. et al, *Cancer,* 57: 571–576 (1986); Chiou, R. et al, *Cancer Res.,* 45: 6140–6146 (1985); Hwang, K. M. et al, *J. Natl. Cancer Inst.,* 76: 849–855 (1986); Colcher, D. et al, *Cancer Res.,* 43: 736–742 (1983); Colcher, D. et al, *Laboratory Research Methods in Biology and Medicine Immunodiagnostics,* New York, Alan R. Liss, pp. 215–258 (1983); Keenan, A. M. et al, *J. Nucl. Med.,* 25: 1197–1203 (1984); Colcher D. et al, *Cancer Res.* 47: 1185–1189 (1987); Esteban, J. M. et al., *Intl. J. Cancer,* 39: 50–59 (1987); Martin, D. T., et al, *Curr. Surg.* 41: 193–194 (1984); Martin, E. W. Jr. et al, *Hybridoma,* 5: S97–S108 (1986); and Martin, D. T. et al, *Am. J. Surg.,* 150: 672–675 (1985); the disclosures of all of which are specifically incorporated herein by reference.

The dosage will vary depending upon the age and weight of the patient, but generally a one time dosage of about 0.1 to 20 mg of antibody-marker conjugate per patient is sufficient. A more preferred dosage is about 1.0 to 2.0 mg of antibody-marker conjugate per patient.

Examples of imaging markers which can be conjugated to the antibody are well known to those skilled in the art and include substances which can be detected by diagnostic imaging using a gamma scanner or hand held gamma probe or Positron Emission Tomography or the like as described in the references cited above and substances which can be detected by nuclear magnetic resonance imaging using a nuclear magnetic resonance spectrometer or the like as described in the references cited above.

Suitable examples of substances which can be detected using a gamma scanner or the like include $^{125}$I, $^{131}$I, $^{123}$I, $^{111}$In, and $^{99m}$Tc. $^{111}$In and $^{99m}$Tc are preferred due to their low energy and suitability for long range detection.

An example of a substance which can be detected using a nuclear magnetic resonance spectrometer or the like is the nuclear magnetic spin-resonance isotope gadolinium (Gd).

C. In Vivo Treatment

In vivo treatment of human carcinomas or metastases thereof using the second generation monoclonal antibodies of the present invention, immunoreactive fragments or recombinants thereof is described in greater detail below.

A pharmaceutically effective amount of a second generation monoclonal antibody of the present invention, immunoreactive fragment or recombinant thereof unconjugated or conjugated to a therapeutic agent is administered to a patient.

Methods of preparing and administering the monoclonal antibody-therapeutic agent conjugate as well as suitable dosages will depend on the age and weight of the patient and the therapeutic agent employed and are well known to or readily determined by those skilled in the art. Representative protocols are described in the references cited below.

Examples of the monoclonal antibody-therapeutic agent conjugates which can be used in therapy include antibodies coupled to radionuclides, such as $^{131}$I, $^{90}$Y, $^{105}$Rh, $^{47}$Sc, $^{67}$Cu, $^{212}$Bi, and $^{211}$At, as described, for example in Goldenberg, D. M. et al, *Cancer Res.,* 41: 4354–4360 (1981); Carrasquillo, J. A. et al, *Cancer Treat. Rep.,* 68: 317–328 (1984); Zalcberg, J. R. et al, *J. Natl. Cancer Inst.,* 72: 697–704 (1984); Jones, D. H. et al, *Int. J. Cancer,* 35: 715–720 (1985); Lange, P. H. et al, Surgery, 98: 143–150 (1985); Kaltovich, F. A. et al, *J. Nucl. Med.,* 27: 897 (1986), Order, S. E. et al., *Int. J. Radiother. Oncol. Biol. Phys.,* 8: 259–261 (1982), Courtenay-Luck, N. et al, *Lancet,* 1: 1441–1443 (1984) and Ettinger, D. S. et al, *Cancer Treat. Rep.,* 66: 289–297 (1982), the disclosure of all of which are specifically incorporated herein by reference; antibodies coupled to drugs or biological response modifiers such as methotrexate, adriamycin, and interferon as described, for example, in Chabner, B. et al, *Cancer, Principles and Practice of Oncology,* Philadelphia, Pa., J.B. Lippincott Co. Vol. 1, pp. 290–328 (1985); Oldham, R. K. et al, *Cancer, Principles and Practice of Oncology,* Philadelphia, Pa., J.B. Lippincott Co., Vol. 2, pp. 2223–2245 (1985); Deguchi, T. et al, *Cancer Res.,* 46: 3751–3755 (1986); Deguchi, T. et al, *Fed. Proc.,* 44: 1684(1985); Embleton, M. J. et al, *Br. J. Cancer,* 49: 559–565 (1984) and Pimm, M. V. et al, *Cancer Immunol. Immunother.,* 12: 125–134 (1982), the disclosure of all of which are specifically incorporated herein by reference; antibodies coupled to toxins, as described, for example, in Uhr, J. W. et al, *Monoclonal Antibodies and Cancer,* Academic Press, Inc., pp. 85–98 (1983), Vitetta, E. S. et al, *Biotechnology and Bio. Frontiers,* Ed. P. H. Abelson, pp. 73–85 (1984) and Vitetta, E. S. et al, *Sci.,* 219: 644–650 (1983), the disclosure of all of which are specifically incorporated herein by reference; heterobifunctional antibodies for example, antibodies coupled or combined with another antibody so that the complex binds both to the carcinoma and effector cells, e.g., killer cells such as T cells, as described, for example, in Perez, P. et al, *J. Exper. Med.,* 163: 166–178 (1986); and Lau, M. A. et al, *Proc. Natl. Acad. Sci. USA,* 82: 8648–8652 (1985); the disclosures of both of which are specifically incorporated herein by reference; and native, i.e., non-conjugated or non-complexed, antibody, as described in, for example, in Herlyn, D. et al, *Proc. Natl. Acad. Sci., USA,* 79: 4761–4765 (1982); Schulz, G. et al, *Proc. Natl. Acad. Sci., USA,* 80: 5407–5411 (1983); Capone, P. M. et al, *Proc. Natl. Acad. Sci., USA,* 80: Z328–7332 (1983); Sears, H. F. et al, *Cancer Res.,* 45: 5910–5913 (1985); Nepom, G. T. et al, *Proc. Natl. Acad. Sci., USA,* 81: 2864–2867 (1984); Koprowski, H. et al, *Proc., Natl. Acad. Sci., USA,* 81: 216–219 (1984); and Houghton, A. N. et al, *Proc. Natl. Acad. Sci., USA,* 82: 1242–1246 (1985) all of which are specifically incorporated herein by reference.

In this method, the monoclonal antibody-therapeutic agent conjugate can be delivered to the carcinoma site thereby directly exposing the carcinoma tissue to the therapeutic agent.

D. Immunohistochemistry and Immunocytochemistry Assays

Immunohistochemistry (hereinafter "IHC") and Immunocytochemistry (hereinafter "ICC") assays for the diagnosis of human carcinomas or metastases thereof or to make differential diagnoses using the second generation monoclonal antibodies of the present invention, are carried out as described in detail below.

A second generation monoclonal antibody of the present invention, is added to a slide containing a 5μ section of a biopsy specimen (for IHC) or cells (for ICC) from body fluid (such as a pleural effusion, ascites sputum, or vaginal fluid). A series of linkers (e.g., biotinylated horse anti-mouse IgG followed by avidin DH:biotinylated horseradish peroxidase complex) and dyes (e.g. diaminobenzidine) are then added to the slides to detect binding of the second generation monoclonal antibody, immunoreactive fragment or recombinant thereof to carcinoma cells in the biopsy or body fluid by a color reaction, i.e., carcinoma cells will look reddish-brown while normal and benign cells will look blue (the background stain). Alternate linkers, dyes, and subsequent color reactions, may of course be applied, as incorporated by reference herein (see Sternberger, L. A. *Immunocytochemistry*, New York, John Wiley & Sons, Second Edition pp. 82–169 (1979)). By this method: (a) carcinoma cells can be detected in biopsy specimens and body fluids as an adjunct to making a diagnosis of cancer, and (b) a differential diagnosis can be made; for example, TAG-72 has been shown to be present in adenocarcinoma of the lung and adenosquamous carcinoma of the lung but not in small cell carcinoma. Thus, detection of binding of the second generation monoclonal antibody of the present invention, immunoreactive fragment or recombinant thereof to a lung biopsy would rule out small cell lung cancer. Furthermore, since TAG-72 has been shown not to be expressed in malignant mesotheltoma, the second generation monoclonal antibody of the present invention, therefore can be used to differentiate adenocarcinoma of the lung from malignant mesothelioma.

The use of IHC and ICC assays for the diagnosis of cancer or to make differential diagnoses are accomplished by methods known to or readily determined by those skilled in the art, as described, for example, in Nuti, M. et al, *Intl. J. Cancer*, 29: 539–545 (1982), Stramignoni, D. et al., *Intl. J. Cancer*, 31: 543–552 (1983), Szpak, C. A. et al., *Acta Cytologica*, 28: 356–367 (1984), Johnston, W. W. et al., *Cancer Res.*, 45: 1894–1900 (1985), Szpak, C. A. et al., *Am. J. Path.*, 122: 252–260 (1986), Thor, A. et al., *J. Natl. Cancer Inst.*, 76: 995–1006 (1986), Martin, S. E. et al, *Am. J. Clin. Path.*, 86: 10–18 (1986), Nuti, M. et al., *Intl. J. Cancer*, 37: 493–498 (1986), Johnson, V. G. et al., *Cancer Res.*, 46: 850–857 (1986), Thor, A. et al, *Cancer Res.* 46: 3118–3124 (1986), Ohuchi, N. et al,, *Intl. J. Cancer*, 38: 643–650 (1986), Johnston, W. W. et al, *Cancer Res.*, 46: 6462–6470 (1986), and Thor, A. et al, *Cancer Res.*, 47: 505–512 (1987), the disclosures of all of which are specifically incorporated herein by reference.

The amount of second generation monoclonal antibody of the present invention, used per slide and the incubation time and temperature may vary, but generally, the IHC and ICC assays are conducted at about 4° C. for about 18 hours using about 40 µg per ml of monoclonal antibody.

E. Activating the Anti-Idiotype Network

Activating the anti-idiotypic network for cancer therapy using the second generation monoclonal antibodies of the present invention, immunoreactive fragments or recombinants thereof is carried out as described in detail below.

A second generation monoclonal antibody of the present invention, immunoreactive fragment or recombinant thereof (designated Ab 1) is administered to a patient at multiple intervals. The immune system of the patient will respond by the generation of antibodies (designated Ab 2) which have binding specificity to the binding site of Ab 1. These anti-idtotype antibodies (Ab 2's) will then elicit the formation of antibodies (designated Ab 3) which have binding specificity to the binding site of Ab 2. The Ab 2 antibodies will be an internal image of the original TAG-72, and thus the Ab 3 antibodies will have binding specificity and potentially destroy a carcinoma producing TAG-72.

The use of monoclonal antibodies to activate the idiotypic network and the procedures used to accomplish this are readily known or readily determined by those skilled in the art, as described, for example, in Ninsonoff, A. et al, *Clin. Immunol. and Path.*, 21: 397–406 (1981), Forstrom, J. W. et al, *Nature*, 303: 627–629 (1983), Kauffman, R. S. et al, *J. Immunol.*, 131: 2539–2541 (1983); Reagen, K. J. et al, *J. Virol.*, 48: 660–666 (1983), Koprowski, H. et al, *Pro. Natl. Acad. Sci.* (*USA*), 81: 216–219 (1984), Herlyn, D. et al, *J. Immunol.*, 143: 1300–1304 (1985), Koprowski, H. et al, *J. Immunol. Meth.* 85: 27–38 (1985), Koprowski, H. et al, *Science*, 232: 100–102 (1985), Greene, M. I. et al, *J. Immunol.*, 137: 2930–2936 (1986), Kohler, H. et al, *J. Immunol.*, 137: 1743–1749 (1986), Notkins, A. L. et al, *J. Exp. Med.*, 163: 1355–1360 (1986), the disclosures of all of which are specifically incorporated herein by reference.

The activation of the anti-idiotypic network can be used to stimulate a patient's immune system so that the patient can mount an active immune response against carcinomas producing TAG-72.

The following examples are provided for illustrative purposes only and are in no way intended to limit the scope of the present invention.

EXAMPLE 1

Preparation of Monoclonal Antibodies

A. Preparation of Immunogen

LS-174T colon carcinoma cells (ATCC No. CRL-188) were grown in Eagle's minimum essential medium with non-essential amino acids supplemented with 10% (v/v) heat-inactivated fetal calf serum, 100 units/ml penicillin and 100 µg/ml streptomycin. The LS-174T cells were tested for the presence of Mycoplasma species and were found to be negative.

Four-week old female athymic mice were inoculated subcutaneously with 1×10$^6$ LS-174T cells in 0.1 ml of culture medium. Carcinoma xenografts were harvested when they reached approximately 1.0 cm in diameter (15–20 days after cell implantation), quick frozen in liquid nitrogen and stored at –70° C. Large carcinoma xenografts were not used due to necrosis.

Thereafter, approximately 3 grams of frozen LS-174T human carcinoma xenograft was homogenized with an Omni Mixer for 45 sec in buffer comprising 20 mM Tris (pH7.2) and 150 mM NaCl (hereinafter "TBS"). The homogenized xenograft was then filtered through glass wool and loaded onto a Sepharose CL-4B column sizing column (Pharmacia, Upsala, Sweden) (5.5×25 cm) which was previously equilibrated in TBS. The column was eluted using TBS (pH 7.2).

7.0 ml fractions were collected and examined in a direct binding assay using 1/10 volume dilutions. More specifically, 50 µl of the dilutions were added to wells of a 96-well polyvinyl chloride microtiter plate (Dynatech Laboratories, Inc., Alexandria, Va.). To minimize nonspecific protein adsorption, the microtiter wells were treated with 100 µl of 5.0% bovine serum albumin (hereinafter "BSA") in phosphate buffered saline, comprising 8.0 mM $Na_2HPO_4$, 1.5 mM $KH_2PO_4$, 2.5 mM KCl, 140 mM NaCl, 0.5 mM $MgCl_2$, 1.0 mM $CaCl_2$, (pH 7.2) (hereinafter "PBS") and incubated for 1 hour at 37° C. Next, the BSA was removed and $^{125}$I-B72.3, prepared as described in Colcher, D. et al, *Cancer Res.*, 44: 5744–5751 (1984) at 50,000 cpm/25 µl per well, was added to each well. Following an overnight incubation at 4° C., unbound $^{125}$I-B72.3 was removed by washing with 1.0% BSA (v/v) in PBS. The bound $^{125}$I-B72.3 was detected by cutting individual wells from the plate and measuring the radioactivity in a gamma counter (RIAgamma, LKB, Bromma, Sweden).

Thereafter, the peak fractions were pooled (130 mls of material), and loaded onto a B72.3 affinity column which was washed with TBS. The B72.3 affinity column was prepared as described in Johnson, V. et al, *Cancer Res.*, 46: 850–857 (1986) and comprised 100 ml of 1,1'-carbonyldiimidazole activated affinity matrix Reacta-Gel HW65F (Pierce, Rockford, Ill.) coupled with 200 mg of B72.3. The column was washed with TBS and the bound protein was eluted with 3.0M NaI in TBS. The column was finally washed with TBS.

5.0 ml fractions were collected and examined in a second direct binding assay carried out as described above. The peak fractions were pooled (92 mls of protein) and dialyzed against 4.0 liters of 20 mM Tris (pH7.2) at 4° C. overnight. The purified TAG-72 thus obtained was concentrated in Aquacide II, sodium salt of carboxymethyl cellulose (Calbiochem, San Diego, Calif.) and used as the immunogen.

B. Immunizations

1. CC Group

For the group designated CC hereinafter, three four-week old BALB/c mice were immunized by intraperitoneal inoculation of 10 μg of TAG-72 purified as described above which had been pre-mixed with an equal volume of complete Freund's adjuvant. After 80 days, the mice received booster doses intraperitoneally of 50 μg of TAG-72 purified as described above which had been pre-mixed with an equal volume of incomplete Freund's adjuvant. Seven days later the mice received 10 μg of TAG-72 in saline, by intravenous inoculation. Spleens were harvested three days later for cell fusion.

2. MATAG Group

For the group designated MATAG hereinafter, two four-week old BALB/c mice were immunized by intraperitoneal inoculation of 50 μg of TAG-72 purified as described above which had been pre-mixed with an equal volume of complete Freund's adjuvant. After seven days, the mice received booster doses intraperitoneally of 50 μg of TAG-72 purified as described above which had been pre-mixed with an equal volume of incomplete Freund's adjuvant. Seven days later the mice received 10 μg of TAG-72 in saline, by intravenous inoculation. Spleens were harvested three days later for cell fusion.

C. Preparation of Hybridomas

Somatic cell hybrids (hybridomas) were prepared using a modification of the method of Herzenberg, L. A. et al, *Handbook of Experimental Immunology*, Oxford, Blackwell pp. 25.1–25.7 (1978). More specifically, single cell suspensions of spleen cells from the immunized mice were made by passing the spleen tissue of the mice through a No. 3 mesh stainless steel screen (B. Fenenco Co., Inc., Norcester, Mass.). The spleen cells and NS-1 mouse myeloma cells (ATCC No. TIB-18) were washed in RPMI-1640 medium, containing 2.0 mM glutamine, 1.0 mM sodium pyruvate, 50 units/ml pentillin, 50 μg/ml streptomycin and 0.25 μg/ml Fungizone, an antimycotic mixture (Grand Island Biological Company, Grand Island, N.Y.). Then, the spleen cells and NS-1 mouse myeloma cells were mixed at a 4:1 ratio, and fused with 50% (v/v) polyethylene glycol (M.W. 1500) (BDH Chemical Ltd., Poole, England). After fusion, individual wells of 96-well microtiter plates (Costar, Cambridge, Mass.) were seeded with $1 \times 10^6$ total cells (0.1 ml) of the cell suspension. Fused cells were then selected for growth with HAT media.

Cloning of hybridoma cell lines was performed by limiting dilution. Specifically, twenty-four wells of a 96-well microtiter plate (Costar, Cambridge, Mass.) were seeded with one of the following concentrations of hybridoma cells: 10 cells/well, 5 cells/well, 1.0 cell/well, or 0.5 cell/well. Mouse thymocytes, derived from the thymus glands of four-week old BALB/c mice, were added to each well as feeder cells at a concentration of $10^6$ cells/well. Wells were seeded at the concentration that eventually resulted in the growth of single cell cultures.

A total of 2,567 initial hybridoma cultures were obtained for the CC group and a total of 2,000 initial hybridoma cultures were obtained for the MATAG group. All hybridoma cell lines selected for further screening were cloned twice.

D. Solid Phase Radioimmunoassays

1. CC Group

The CC group was assayed in a SPRIA using the cell extacts from a metastatic breast carcinoma and normal spleen and liver.

More specifically, 50 μl of the cell extracts (5 μg) were added to each well of a Cooke round bottom polyvinyl chloride microtiter (Dynatech Laboratories, Alexandria, Va.) plate and allowed to dry. To minimize non-specific protein absorption, microtiter wells were treated with 100 μl of 5.0% (v/v) BSA in PBS and incubated with the sample covered for 1 hour. This and all subsequent incubations were at 37° C. The BSA was then removed and the wells were washed one time with 1.0% (v/v) BSA in PBS. Next, 50 μl of hybridoma supernatant was added per well. After a 1 hour incubation, the unbound immunoglobulin was removed by washing the plates three times with 1.0% (v/v) BSA in PBS at 100 μl/well/wash.

To determine antibody binding, the wells were then incubated with 25 μl of $^{125}$I-goat-anti-mouse IgG(γ chain specific) (Kirkegaard & Perry, Gaithersburg, Md.) at 75,000 cpm/25 μl per well for 1 hour at 37° C. The supernatant was aspirated and the plates were washed four times with 1.0% (v/v) BSA in PBS at 100 μl/well/wash.

The plates were then subjected to autoradiography using Kodak XAR film and Dupont Lightning-Plus intensifying screens. The films were developed after 16 hours at −70° C. The bound cpm were also detected by cutting the individual wells from the plate and measuring the cpm in a gamma counter.

The results yielded 433 CC cultures which had binding specificity, in the SPRIA, to the carcinoma extract but not to the normal extracts.

All of these 433 CC cultures were then assayed, in a SPRIA as described above, using the cell extracts shown in Table 1 below.

Table 1

Primary colon carcinoma
Metastatic breast carcinoma
Normal kidney
Normal liver
Normal colon
Normal stomach
Normal bone marrow
Normal lung
Normal thyroid
Polymorphonuclear leukocyte
Red blood cell The results yielded 99 CC cultures which had binding specificity, in the SPRIA, to the carcinoma extracts but not to the normal extracts listed in Table 1 above.

Next, all of the 99 cultures were cloned into 9,504 wells and each well was checked for growth of a single colony. Those with a single colony were selected for further assay. Those that were selected were assayed, in a SPRIA as described above, using extracts of a metastatic breast carcinoma and primary colon carcinoma as well as normal liver.

The colonies that had binding specificity, in the SPRIA, to the carcinoma extracts but not to normal liver extract were recloned and again assayed for binding specificity, in the SPRIA, to the colon carcinoma extract but not to the normal liver extract. This resulted in the generation of 29 CC monoclonal antibodies which had binding specificity to the colon carcinoma but not the normal liver extracts (see FIG. 1).

All of the 29 CC monoclonal antibodies shown in FIG. 1 exhibit binding specificity to extracts of colon adenocarcinoma, but lack binding specificity to extracts of the following normal and/or benign tissues: colon (minimal binding specificity to superficial goblet cells), ovary, stomach (minimal binding specificity to goblet cells of intestinal metaplasia), endocervix (minimal binding specificity to glandular epithelium), brain, kidney, spleen, lung (minimal binding specificity to epithelium), skin (minimal binding specificity to sebaceous glandular epithelium), liver, prostate, uterus (binding specificity to secretory phase endometrium only), adrenal, pancreas, heart, lymph node, bone marrow, breast and small intestine (minimal binding specificity to superficial mucosal cells).

Of the 29 CC monoclonal antibodies so produced, the hybridomas producing preferred monoclonal antibodies have been deposited at the American Type Culture Collection under CC 49 (ATCC No. HB 9459), CC 83 (ATCC No. HB 9453), CC46 (ATCC No. HB 9458), CC 92 (ATCC No. HB 9454), CC 30 (ATCC No. HB 9457), CC 11 (ATCC No. HB 9455), and CC 15 (ATCC No. HB 9460).

2. MATAG Group

The MATAG group was assayed in a SPRIA essentially as described above for the CC group using a 1/80 dilution per well of TAG-72 in PBS except that to detect binding of antibody, 50 µl of rabbit-anti-mouse IgM (Cooper Biomedical Malvern, Pa.) was added to each well. The plates were incubated for 1 hour at 37° C. after which time $^{125}$I-labeled Protein A (SPA) (Pharmacia, Upsala, Sweden) at 50,000 cpm/25 µl was added per well and again allowed to incubate at 37° C. for 1 hour. The unbound SPA was removed by extensive washing with 1.0% (v/v) BSA in PBS.

Of the 2000 MATAG cultures assayed using TAG-72 and PBS, 110 were found to have binding specificity to TAG-72. Further cloning and assaying in a SPRIA as described above, using TAG-72 yielded 34 cultures which had binding specificity with a colon cancer extract and TAG-72 but not a normal liver extract. These were cloned into 3,264 wells and approximately 20 wells of each of the original 34 cultures were assayed, in a SPRIA as described above, using TAG-72 and PBS. This yielded 23 cultures which had binding specificity to TAG-72. The 23 cultures were subsequently grown up and further assayed, in a SPRIA as described above, for lack of binding specificity to normal spleen and normal liver and binding specificity to a metastatic breast carcinoma extract, as well as being assayed, in a SPRIA as described above, using TAG-72 and PBS. The results yielded 15 cultures which exhibited binding specificity to the carcinoma extract and TAG-72 but not to the normal extracts. These cultures were then recloned and reassayed, in a SP, RIA as described above, to produce 15 MATAG monoclonal antibodies (see FIG. 1).

All of the MATAG monoclonal antibodies shown in FIG. 1 exhibit binding specificity to extracts of ovarian carcinoma, colon adenocarcinoma, infiltrating ductal carcinoma of the breast, non-small cell lung carcinoma, but lack binding specificity to extracts of the following normal and/or benign tissues: colon (minimal binding specificity to mucosal goblet cells), ovary, benign effusions (minimal binding specificity to mucosal goblet cells), ovary, benign effusions (minimal binding specificity to lymphocytes and mesothelial cells), lung (minimal binding specificity to bronchial epithelium), spleen, liver, breast, kidney, bone marrow, stomach (minimal binding specificity to superficial epithelium), skin, nerve, parathyroid, heart, pancreas, lymph node, adrenal, thyroid, small intestine (minimal binding specificity to superficial mucosa), brain, gall bladder, cervix, uterus (binding specificity to secretory phase of endometrium only), endocervix (minimal binding specificity to endocervical glandular epithelium), bladder, appendix, fallopian tube, muscle, salivary gland, thymus, testis, and esophagus.

Of the 15 MATAG monoclonal antibodies so produced, the hybridoma producing MATAG 12 is preferred and has been deposited at the American Type Culture Collection under MATAG 12 (ATCC No. HB 9456).

EXAMPLE 2

Isotyping Assay

1. CC Group

For the CC group, 50 µl of polyclonal anti-mouse IgG (Jackson Immunoresearch Laboratories, Inc., West Grove, Pa.) was absorbed onto a 96-well polyvinyl chloride (Dynatech Laboratories, Alexandria, Va.) microtiter plate. The IgG was diluted with PBS. The plates were incubated overnight at 37° C. The following day, 100 µl of 5.0% (w/v) BSA in PBS was added to each well and allowed to incubate for 1 hour to minimize non-specific absorption. The wells were then washed with 1.0% (w/v) BSA in PBS. 50 µl of undiluted CC culture supernatant was added to each of two wells. The plates were again incubated for 1 hour at 37° C. after which time they were washed 3 times with 1.0% (w/v) BSA in PBS. Rabbit-anti-mouse $IgG_1$, $IgG_{2a}$, $IgG_{2b}$, $IgG_3$, IgM, IgA (Cooper Biomedical, Malvern, Pa.) DC-12 (NIH, NCI, LTIB) and control 1.0% (w/v) BSA in PBS were added at 50 µl per well. Following a 1 hour incubation, the plates were washed 3 times as described above. Then 50,000 cpm of $^{125}$I-labeled Protein A (SPA) were added to each well, incubated for 1 hour, washed 4 times with 1.0% (w/v) BSA in PBS and the cpm per well was counted in a gamma counter. The results are shown in FIG. 1.

2. MATAG Group

For the MATAG group, isotypes were determined by parallel assays essentially as described above for the CC group. However, for detection, one assay used $^{125}$I-labeled goat-anti-mouse IgG (Kirkegaard & Perry, Gaithersburg, Md.) and the other assay used $^{125}$I-labeled goat-anti-mouse IgM (Kirkegaard & Perry, Gaithersburg, Md.) in place of $^{125}$I-labeled Protein A (SPA).

The MATAG group was further characterized by High Performance Liquid Chromatography (hereinafter "HPLC") analysis for their pentameric structure. HPLC analysis was performed using a Zorbax GF-450 column, 0.94×25 cm (Dupont, Wilmington, Del.), equilibrated in 0.2M sodium phosphate, (pH 6.8). 100 µl MATAG culture supernatant was loaded on the column and the column was run at a flow rate of 0.5 ml/min, 0.5 ml fractions were collected at 1 min intervals. The fractions were analyzed for isotypes as described above. The results are shown in FIG. 1.

EXAMPLE 3

Competition RIA

Competition RIAs were performed to determine whether B72.3 and the CC monoclonal antibodies of the present invention recognize different antigenic determinants. More specifically, B72.3 and the CC monoclonal antibodies were assayed for their ability to compete for the binding of $^{125}$I-labeled B72.3 to an extract of LS-174T colon carcinoma cells in the following manner.

Figure 2A:
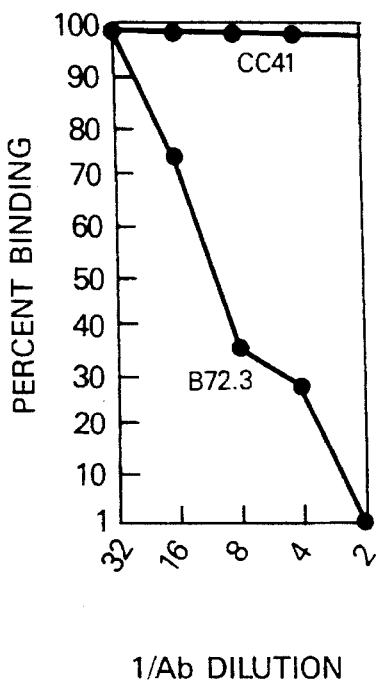
FIG. 2A is an analysis of the binding specificity of monoclonal antibody CC41 to LS-174T colon carcinoma cell extract in a competition RIA with B72.3.

5.0 µg of LS-174T colon carcinoma cell extract was absorbed in each well of a polyvinyl chloride microtiter plate (Dynatech Laboratories, Alexandria, Va.) and varying amounts of competing CC monoclonal antibody (from 100 µg/µl to 0.004 µg/µl) was added to saturate the binding sites. After incubation for six hours at 4° C., 50,000 cpm/25 µl of $^{125}$I-B72.3, was added to each well and incubated for 12 hours at 4° C. Bound $^{125}$I-B72.3 was determined by cutting individual wells and measuring cpm in the wells in a gamma counter. The cpm in the wells pre-incubated with saturating amounts of B72.3 as a competitor was considered 100% competition. The results are shown in FIGS. 2A, 2C, 2E and 2G. In FIG. 2A, CC 41 was used as the competing antibody. In FIG. 2C, CC 60 was used as the competing antibody. In FIG. 2E, CC 83 was used as the competing antibody. In FIG. 2G, CC 49 was used as the competing antibody.

As shown in FIGS. 2A and 2C, CC 41 and CC 60 did not compete at all with B72.3. This demonstrates that CC 41 and CC 60 have binding specificity for a different epitope on TAG-72 than B72.3. As shown in FIGS. 2E and 2G, CC 83 and CC 49 partially compete with B72.3. This demonstrates that the epitopes recognized by CC 83 and CC 49 share partial (but not complete) homology with the B72.3 epitope on the TAG-72 molecule, or that the CC 83 and CC 49 epitopes are distinct from but near the B72.3 epitope, resulting in steric hindrance.

Thereafter, competition RIAs were performed to determine whether CC 49 recognizes the same or different antigenic determinants than B72.3, CC 30, CC 46 and CC 83. More specifically, these monoclonal antibodies were assayed for their ability to compete for the binding of $^{125}$I-labeled CC 49 to an extract of LS-174T colon carcinoma cells as described above. The results obtained are shown in FIG. 3. FIG. 3 demonstrates that (1) the epitopes on TAG-72 recognized by monoclonal antibodies CC 46 and B72.3 share little or no homology with the epitope recognized by monoclonal antibody CC 49; (2) the epitope recognized by CC 83 shares considerable homology with that recognized by CC 49 but is not identical as revealed by the displacement of the CC 83 curve; and (3) the epitope recognized by monoclonal antibody CC 30, shares partial homology to that recognized by CC 49, or is distinct from that of CC 49 but is in proximal location resulting in steric hindrance.

EXAMPLE 4

Binding Affinity

The binding affinities (affinity constants) of the second generation monoclonal antibodies of the present invention to TAG-72 were determined by a SPRIA using a modification of the procedure of Heyman, B. et al, *J. Immunol. Methods*, 68: 193–204 (1984). More specifically, 30 µl of purified TAG-72 diluted in PBS at a concentration of 280 units/ml (units determined as described in Paterson, A. J. et al, *Intl. J. Cancer*, 37: 659–666 (1986)) were dried in 96-well polyvinyl chloride microtiter plates (Dynatech Laboratories, Alexandria, Va.). Any remaining non-specific active groups were blocked with 5.0% (v/v) BSA in PBS. Then, 20 µl of 1:1.5 serial dilutions of the purified monoclonal antibody (purified as described in Colcher, D. et al, *Cancer Res.*, 44: 5744–5751 (1984), shown in Table 2 below, starting at 1.0 µg/ml were added to the wells. After incubating overnight at 4° C., the plates were washed three times with 1.0% (v/v) BSA in PBS. Next, $^{125}$I-labeled goat anti-mouse IgG (Kirkegaard & Perry, Gaithersburg, Md.) at 75,000 cpm/25 µl per well was added and left to react for 1 hour at 37° C. After washing three times with 1.0% (v/v) BSA in PBS the cpm in the individual wells were counted as described above.

In order to convert the cpm values to concentration of bound monoclonal antibody, the remaining free monoclonal antibodies in the supernatant, which had been incubated with TAG-72 but not bound thereto, were incubated on another 96-well polyvinyl chloride microtiter plate which had been precoated with 4.0 µg/ml of sheep anti-mouse IgG (Jackson Immunoresearch Laboratories, Inc., West Grove, Pa.) and detected with $^{125}$I-labeled goat anti-mouse IgG (Kirkegaard & Perry, Gaithersburg, Md.). In this manner, the concentration at which there was no free monoclonal antibodies remaining in the supernatant was determined for each monoclonal antibody. From these data computer curves were generated to determine the binding affinity constant of each monoclonal antibody. The results are shown in Table 2 below.

TABLE 2

Binding Affinity Constants Measured Using TAG-72

| Purified Antibody | Affinity Constant ($\times 10^9$ M) |
|---|---|
| B72.3 | 2.54 |
| CC-46 | 3.64 |
| CC-30 | 8.15 |
| CC-15 | 9.13 |
| CC-29 | 9.49 |
| CC-92 | 14.26 |
| CC-49 | 20.58 |
| CC-83 | 27.72 |

Table 2 demonstrates that the second generation monoclonal antibodies CC 46, CC 30, CC 15, CC 29, CC 92, CC 49 and CC 83 all have higher binding affinity constants than the first generation monoclonal antibody B72.3.

The CC group was assayed in a SPRIA using the cell extracts from the LS174T cell line and a metastatic breast carcinoma. 50 µl of the cell extract (5 µg) was added to each well of a Cooke round bottom polyvinyl chloride microtiter plate (Dynatech Laboratories, Alexandria, Va.) and allowed to dry. To minimize non-specific protein absorption, microtiter wells were treated with 100 µl of 5.0% (v/v) BSA in PBS and incubated covered for 1 hour. This and all subsequent incubations were at 37° C. The BSA was then removed and the wells were washed one time with 1.0% (v/v) BSA in PBS. Next, 50 µl of hybridoma supernatant and 1:5 dilutions of the supernatant fluid was added per well. After a 1 hour incubation, the unbound immunoglobulin was removed by washing the plates three times with 1.0% (v/v) BSA in PBS at 100 µl/well/wash.

To determine antibody binding, the wells were then incubated with 25 µl of $^{125}$I-goat-anti-mouse IgG (gamma chain specific) (Kirkegaard & Perry, Gaithersburg, Md.) at 75,000 cpm/25 µl per well for 1 hour at 37° C. The supernatant was aspirated and the plates were washed four times with 1.0% (v/v) BSA in PBS at 100 µl/well/wash. The bound cpm were detected by cutting the individual wells from the plate and measuring the cpm in a gamma counter.

Figure 2B:
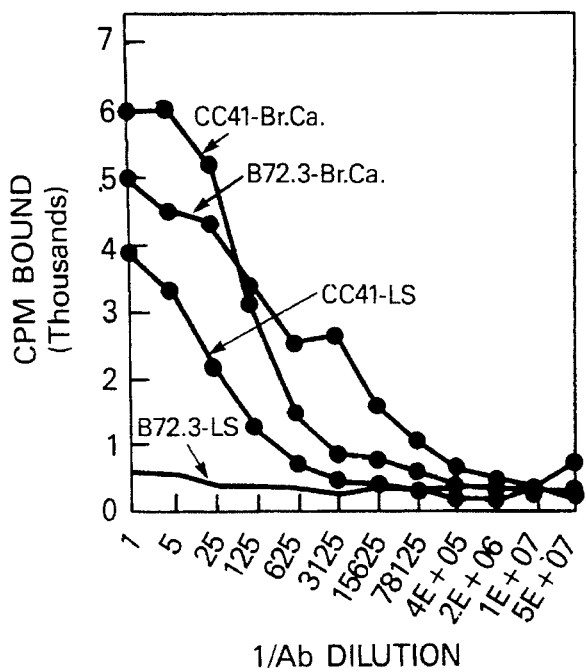
FIG. 2B is a quantitative analysis of the binding specificities of monoclonal antibodies B72.3 and CC41 to LS174T colon carcinoma cell line extract (LS) and a breast carcinoma biopsy extract (Br. Ca.) in a SPIRA.
Figure 2C:
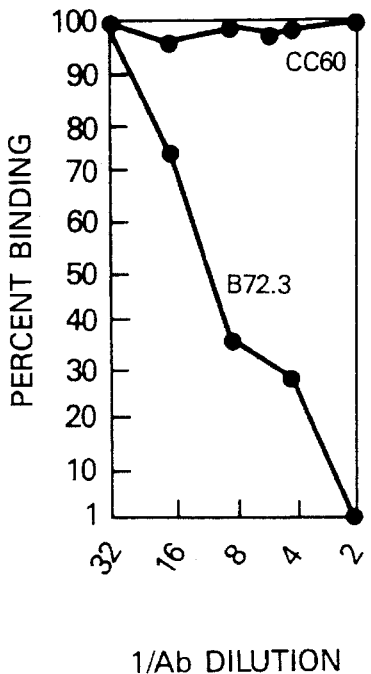
FIG. 2C is an analysis of the binding specificity of monoclonal antibody CC60 to LS-174T colon carcinoma cell extract in a competition RIA with B72.3.
Figure 2D:
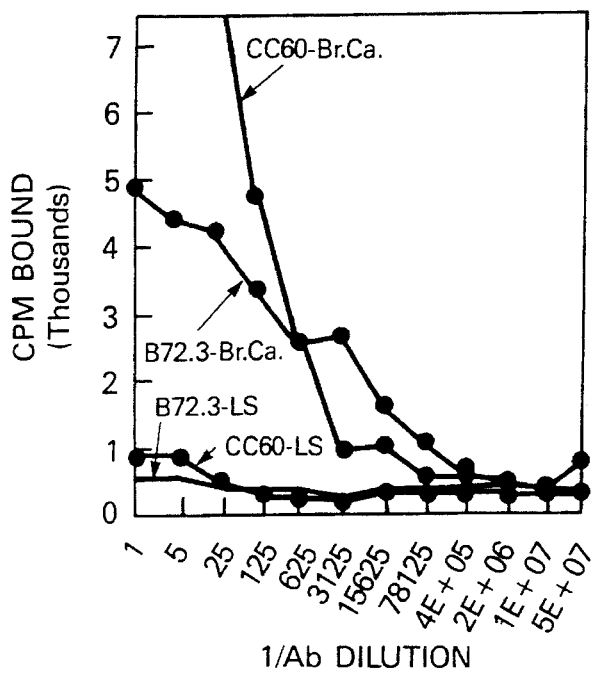
FIG. 2D is a quantitative analysis of the binding specificities of monoclonal antibodies B72.3 and CC60 to LS-174T colon carcinoma cell line extract (LS) and a breast carcinoma biopsy extract (Br. Ca.) in a SPRIA.
Figure 2E:
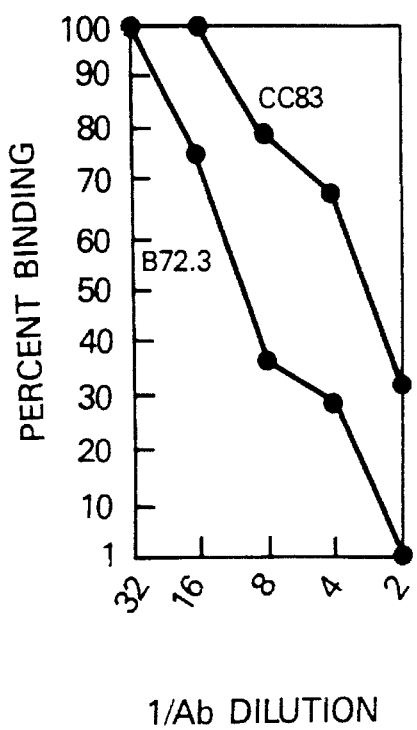
FIG. 2E is an analysis of the binding specificity of monoclonal antibody CC83 to LS-174T colon carcinoma cell extract in a competition RIA with B72.3.
Figure 2F:
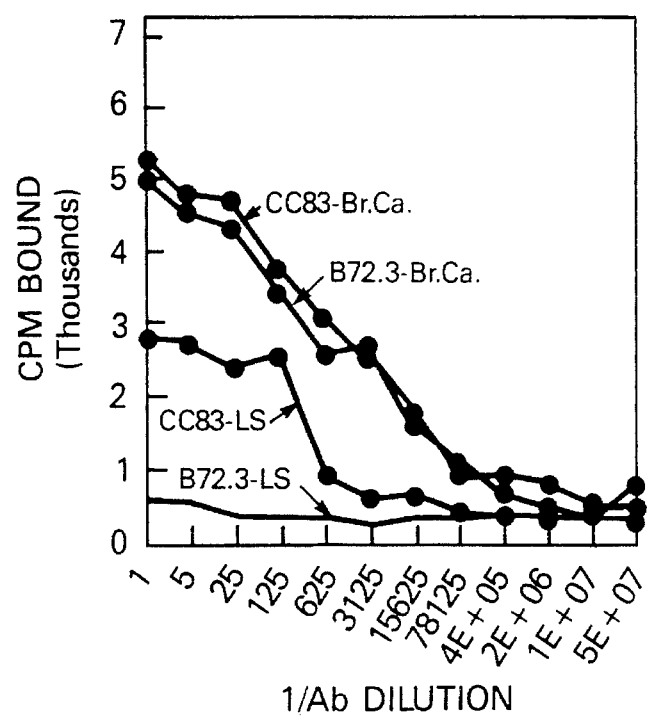
FIG. 2F is a quantitative analysis of the binding specificities of monoclonal antibodies B72.3 and CC83 to LS-174T colon carcinoma cell line extract (LS) and a breast carcinoma biopsy extract (Br. Ca.) in a SPRIA.
Figure 2G:
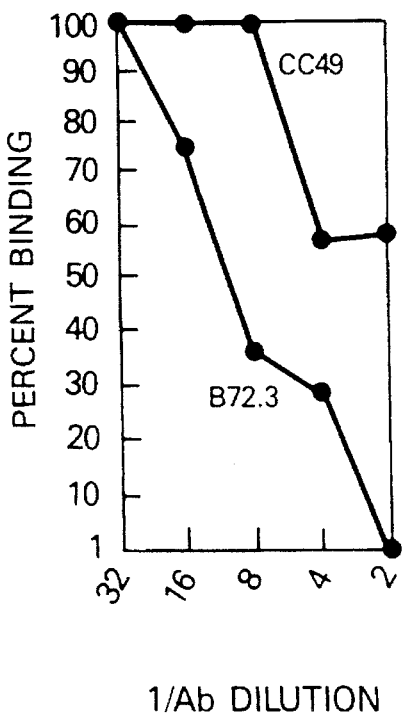
FIG. 2G is an analysis of the binding specificity of monoclonal antibody CC49 to LS-174T colon carcinoma cell extract in a competition RIA with B72.3.
Figure 2H:
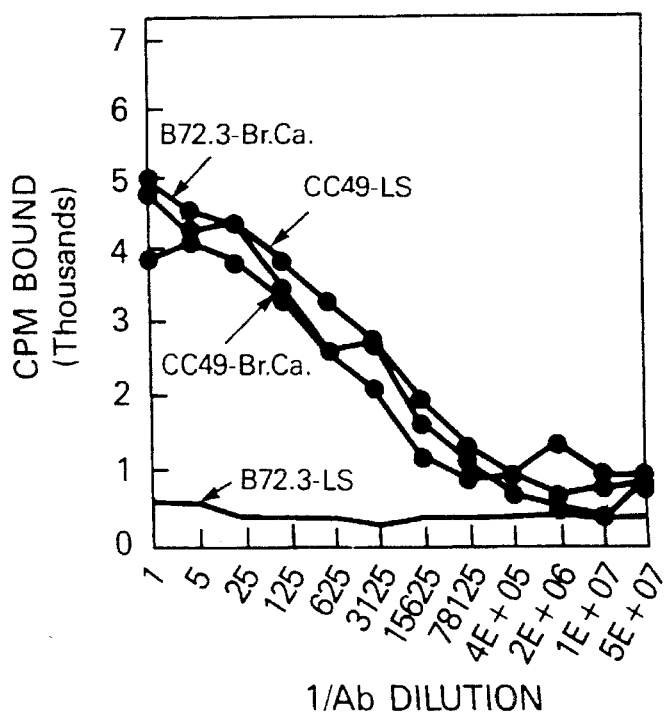
FIG. 2H is a quantitative analysis of the binding specificities of monoclonal antibodies B72.3 and CC49 to LS-174T colon carcinoma cell line extract (LS) and a breast carcinoma biopsy extract (Br. Ca.) in a SPRIA.

As shown in FIG. 2B, CC 41 reacts with the LS extract but B72.3 does not. Note, FIG. 2B and Table 2 demonstrates that CC 41 has a higher binding affinity (slope of the curve) to the Br. Ca. than B72.3. FIG. 2D demonstrates that although CC 60 does not have binding specificity to the LS extract like B72.3, CC 60 has a higher binding affinity (slope of the curve) to the Br. Ca. than B72.3. FIG. 2F demonstrates that CC 83 and B72.3 have similar binding properites to the Br. Ca. extract but that CC 83 has high binding affinity to the LS extract while B72.3 does not. FIG. 2H demonstrates that CC 49 has high binding affinity to both the LS and Br. Ca. extracts while B72.3 has essentially no binding affinity to the LS extract.

EXAMPLE 5

Western Blotting

40 μg of LS174T cell extracts or an extract of a human breast carcinoma diluted in SDS-PAGE sample buffer comprising 0.125M Tris-HCl (pH 6.8) 4.0% (w/v) SDS, 20% (v/v) glycerol and 10% (v/v) 2-mercaptoethanol, loaded onto a 3 to 12% (v/v) linear gradient SDS-PAGE. After electrophoresis for 8 hours at 5 milliamps/gel at 9° C. the gels were treated with transfer buffer comprising 25 mM Tris-HCl (pH 8.3), 192 mM glycine, 20% (v/v) methanol with 4M urea and 0.5% Triton-X-100 for 1 hour at room temperature. The gel was then equilibrated with transfer buffer and the proteins were transferred to nitrocellulose paper (0.45-μm pore size) at 4° C. for 16 hours at 30 V. Then, the nitrocellulose paper was incubated with 5.0% (w/v) BSA with 0.05% (v/v) Tween-20 in PBS for 3 hours at room temperature and washed with 0.05% (v/v) Tween-20 in PBS. Next, 10 ml of hybridoma tissue culture supernatant of all the CC and MATAG monoclonal antibodies were added, and incubation continued for 2 hours at room temperature with gentle agitation. After washing with PBS containing 0.05% (v/v) Tween-20, the nitrocellulose paper was incubated for 1 hour at room temperature with $^{125}$I-labeled goat-anti-mouse IgG (Kirkegaard & Perry, Gaithersburg, Md.). The nitrocellulose paper was then extensively washed overnight and exposed to Kodak XAR-5 X-ray film with a DuPont Lightning Plus intensifying screen at −70° C. for 2 hours. For all experiments NS-1 tissue culture supernatant was used as a negative control.

The Western blotting analysis demonstrated the reactivity of the CC MATAG antibodies to a difuse band beginning at the interface of the stacking gel with the 5–12% resolving gel that penetrated the resolving gel approximately 1 cm. This difuse band is consistent with the high molecular weight TAG-72 mucin-like molecule. The high molecular weight band was observed with all the CC and MATAG antibodies tested and detected in both the LS174T cell line extract and the human breast carcinoma metastases extract.

EXAMPLE 6

Immunoperoxidase Studies 5.0μ sections of formalin-fixed or frozen sections of tissue on slides were used. Fixed tissues were deparaffinized in xylene and hydrated in graded H$_2$O/ethanol rinses. A 15 minute incubation with 0–3% (v/v) H$_2$O$_2$ in in methanol was used to block any endogenous peroxidase activity. After rinsing in PBS without Ca$^{+2}$ and Mg$^{+2}$, the slides were incubated with a 1:10 (v/v) dilution of normal goat serum for the MATAG designated antibodies for 15 minutes. This incubation and all subsequent incubations were carried out at room temperature with the exception of the primary MATAG) antibody which was a 16 hour incubation at 4° C.

The normal blocking serum was removed and undiluted tissue culture supernatant of the monoclonal antibody was placed on the tissue sections and the slides were incubated overnight. The supernatant IgM was removed and the slides were rinsed for 15 minutes in PBS wihout Ca$^{+2}$ and Mg$^{+2}$. For the MATAG designated antibodies at 1:167 (v/v) dilution of biotinylated goat anti-murine IgM (Vector Laboratories, Inc.), was added to each of the tissue sections and allowed to incubate for 30 minutes. The slides were again rinsed in PBS without Ca$^{+2}$ and Mg$^{+2}$ and then incubated for 30 minutes with ABC (Vector Labortories, Inc.) peroxidase at room temperature. After another PBS rinse, 0.06% (v/v) 3,3' diaminobenzidine (Sigma Chemical Co., St. Louis, Mo.) with 0.01% (v/v) H$_2$O$_2$ was added for 5 minutes. The sections were rinsed briefly in water, counterstained with hematoxylin, dehydrated in graded ethanol/H$_2$O rinses, cleared (eliminating residual H$_2$O) in xylene, mounted with Permount (histologic mounting medium [Fisher Scientific Co.]) under a coverslip, and examined with a light microscope. Each section was evaluated for the presence of reddish-brown diaminobenzidine precipitate indicative of monoclonal antibody binding. The approximate percentage of positive carcinoma cells was assigned according to the number of carcinoma cells positive with each monoclonal antibody divided by the total number of carcinoma cells times 100. The results are shown in Table 3 below.

TABLE 3

Binding Specificity of B72.3 vs. MATAG-12 in an Immunoperoxidase Assay of Tissue Sections

| | Percent MAb Reactive Carcinoma Cells | |
|---|---|---|
| | B72.3 | MATAG-12 |
| Ovarian Cancer 1 | 6 | 80 |
| Ovarian Cancer 2 | 5 | 25 |
| Ovarian Cancer 3 | 10 | 55 |
| Colorectal Cancer 1 | 10 | 60 |
| Colorectal Cancer 2 | 40 | 95 |

As shown in Table 3, the percent carcinoma cells reactive with B72.3 is considerably lower than that for MATAG-12. This demonstrates that MATAG-12 has a higher binding specificity for the above carcinomas and thus is more useful in immunohistochemical or immunocytochemical assays, as well as in in vivo diagnosis and therapy of cancer.

EXAMPLE 7

In Vivo Carcinoma Targeting

The monoclonal antibodies shown in Table 4 below were labeled with Na$^{125}$I using Iodogen (Pierce Chemical, Rockford, Ill.). More specifically, 40 μg of monoclonal antibody shown in. Table 4 below were adjusted to 0.1 ml 0.1M sodium phosphate buffer (pH 7.2) and then added to a 12 cm×75 cm glass tube coated with 20 μg of Iodogen followed by addition of 0.5 mCi of Na$^{125}$I (New England Nuclear, Boston, Mass.). After a 2 min incubation at room temperature, the protein was removed from the insoluble Iodogen, and the unincorporated $^{125}$I was separated from the antibody by gel filtration through a 10 ml column Sephadex G-25 with a buffer comprising 10 mM sodium phosphate, pH 7.2. The labeled monoclonal antibody in the void was pooled and dialyzed against 10 mM sodium phosphate buffer (pH 7.2) containing 5.0 mM NaI. The iodination protocol yielded labeled IgG monoclonal antibody with a specific activity of 5.0 to 15 μCi/μg (approximately 8.0 to 25×10$^6$ cpm/μg).

Female athymic mice (nu/nu) on a BALB/c background were obtained from Charles River, Inc., or the Frederick Cancer Research Facility at approximately 4 weeks of age. One week later, mice were inoculated subcutaneously (0.1 ml/mouse) with the LS-174T human colon carcinoma cells ($1\times10^6$ cells/animal).

Athymic mice bearing carcinomas 0.3 to 1.5 cm in diameter, approximately 2 to 3 weeks after inoculation of the cells were given injections intraperitoneally of 1.5 µCi (0.1 µg) in PBS of the monoclonal antibodies shown in Table 4 below, which had been iodinated as described above. Groups of five mice were sacrificed at varying times by exsanguination, the carcinoma and normal tissues were excised and weighed, and the cpm were measured in a gamma counter. The cpm/mg of each tissue was then determined and compared to that found in the carcinoma. The results are shown in Table 4 and FIGS. 4A and 4B.

TABLE 4

Percent Injected Dose Per Gram of $^{125}$I-labeled Antibody*

| Tissue | B72.3 | CC11 | CC46 | CC30 | CC92 | CC83 | CC49 |
|---|---|---|---|---|---|---|---|
| Carcinoma | 6.6 | 26.6 | 13.2 | 23.1 | 12.4 | 22.9 | 23.4 |
| Liver | 0.8 | 1.2 | 0.5 | 0.8 | 0.8 | 0.7 | 1.2 |
| Spleen | 0.5 | 1.1 | 0.5 | 1.0 | 1.0 | 0.7 | 1.2 |
| Kidney | 0.6 | 1.1 | 0.4 | 1.0 | 1.0 | 0.7 | 0.4 |
| Lung | 1.4 | 2.4 | 1.1 | 2.1 | 2.0 | 1.8 | 0.6 |
| Blood | 2.9 | 6.2 | 2.1 | 4.1 | 3.8 | 4.6 | 1.1 |

*At 168 hours post monoclonal antibody administration.

Figure 4A:
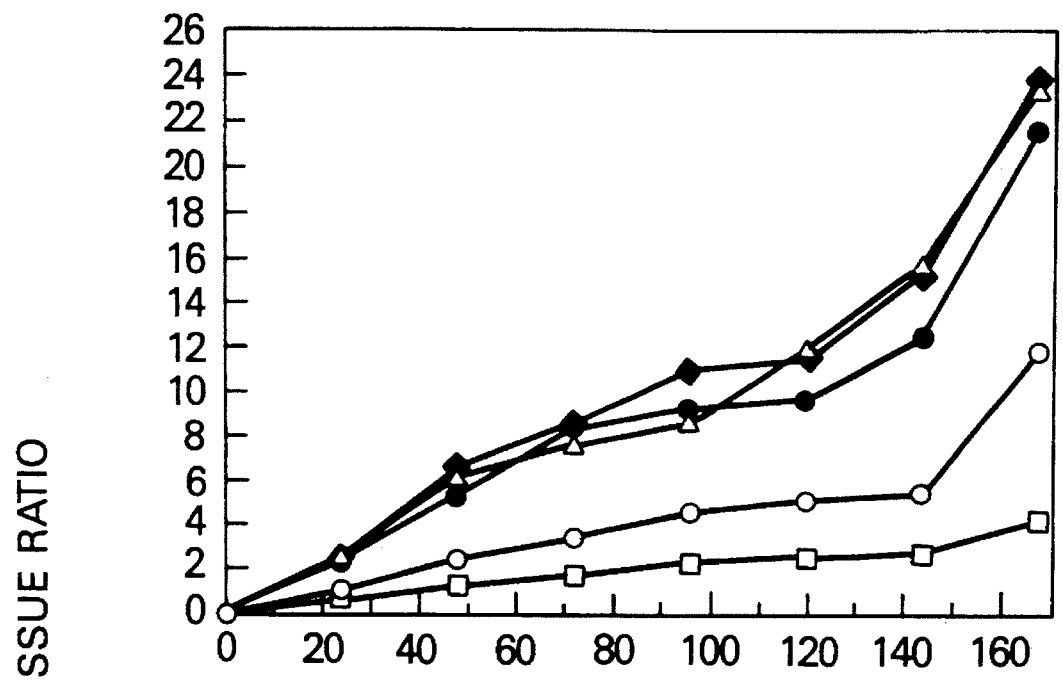
FIG. 4A is an analysis of the in vivo targeting of a LS-174T colon carcinoma xenograft with monoclonal antibody CC11.
Figure 4B:
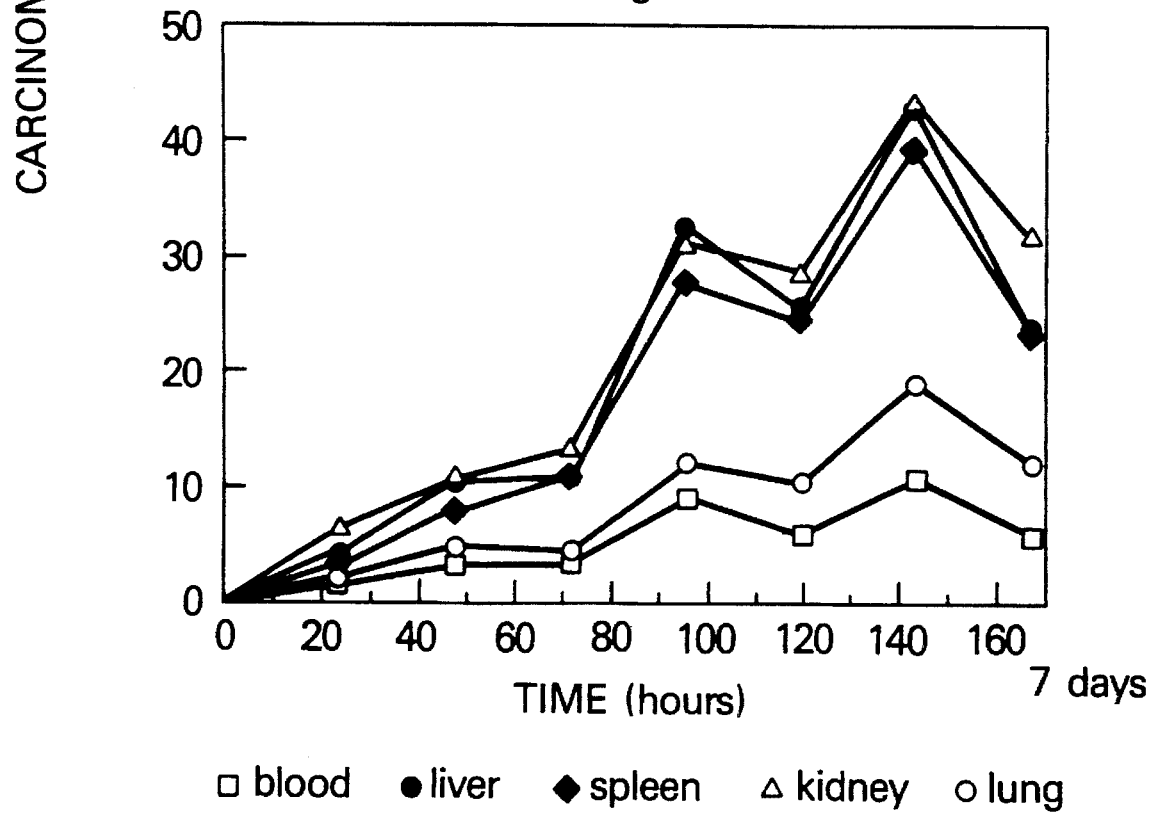
FIG. 4B is an analysis of the in vivo targeting of a LS-174T colon carcinoma xenograft with monoclonal antibody CC46.

As shown in Table 4, the percent of injected dose to tumor for B72.3 is considerably lower than that for the CC antibodies of the present invention. Even though monoclonal antibody CC 46 has only a slightly higher affinity constant than B72.3, Table 4 shows that CC 46 is clearly more efficient in targeting the human tumor in-situ than is B72.3. This demonstrates that the second generation monoclonal antibodies of the present invention are more efficient for in vivo carcinoma targeting than monoclonal antibody B72.3 and thus are more useful in in vivo diagnosis and therapy of cancer. FIGS. 4A and 4B show the different binding kinetics and carcinoma/normal tissue ratios at various time points for CC 11 and CC 46, respectively. FIGS. 4A and 4B demonstrate that these monoclonal antibodies have the ability to bind the carcinomas efficiently and stay bound to the carcinomas over a prolonged time (i.e., at least 7 days).

EXAMPLE 8

Fragmentation of Monoclonal Antibodies

Biodistribution studies both in animal models and in clinical trials have demonstrated that intact IgG may not be the best form of the antibody molecule to obtain optimal tumor localization with minimal background in normal organs. As a result, studies were undertaken to fragment the second generation monoclonal antibodies of the present invention and B72.3 with pepsin as described in Colcher, D. et al, *Cancer Res.*, 43: 736–742 (1983). The resulting fragments were radiolabeled with $^{125}$I as described above and tested for binding specificity in a SPRIA as described above, using a LS-174T colon carcinoma cell extract. The results are shown in Table 5.

TABLE 5

Binding Specificity of Immunoreactive F(ab')$_2$ Fragments

| F(ab')$_2$ Fragment | Binding Specificity to LS-174T colon carcinoma cell extract |
|---|---|
| B72.3 | <2% |
| CC49 | 50% |
| CC46 | 70% |

As shown in Table 5, F(ab')$_2$ fragments of CC 49 were able to bind greater than 50% of the input counts in a SPRIA using limiting amounts of antigen and CC 46 fragments bound over 70% of the input activity while fragments obtained from B72.3 essentially lack all immunoreactivity, i.e, maintained less than 2.0% binding specificity.

A pharmaceutical composition comprising the second generation antibodies of the present invention in a pharmaceutically acceptable, non-toxic, sterile carrier such as physiological saline, non-toxic buffers and the like, now also becomes possible. The amount of said antibodies in the pharmaceutical composition should be sufficient to achieve effective binding with the antigens against which said antibodies have specific affinity or neutralization reactivity. The pharmaceutical composition may be administered in a single or multiple dosage with other adjuvants or additives, if necessary, in any suitable manner to the host in need of said antibodies.

While this invention has been described in detail and with reference to specific embodiments thereof, it will be apparent to one skilled in the art that various changes and modifications could be made therein without departing from the spirit and scope thereof.

What is claimed is:

1. A second generation monoclonal antibody, an immunoreactive fragment or an antigen binding recombinant thereof, which specifically binds both TAG-72 and LS174T cell line antigen but which does not substantially bind normal adult human tissues, wherein said monoclonal antibody has a binding affinity of greater than $3\times10^9 M^{-1}$ for TAG-72, and wherein said monoclonal antibody is CC49 (ATCC CRL 9459) or CC83 (ATCC CRL 9453) or specifically binds to an epitope specifically bound by CC49 or CC83.

2. The second generation monoclonal antibody of claim 1, wherein said antibody has about 50% more efficiency than B72.3 antibody in targeting human carcinomas in-situ.

3. The second generation monoclonal antibody of claim 1, wherein said antibody exhibits 0–30% competition with B72.3.

4. The second generation antibody of claim 1, wherein said antibody is of an isotype selected from the group consisting of IgG$_{2a}$, IgG$_{2b}$, IgG$_3$ and IgM.

5. The second generation antibody of claim 1, wherein said antibody is conjugated to a label, a tumor detecting marker or to a therapeutic agent.

6. The second generation antibody of claim 5, wherein said label is selected from the group consisting of a radioisotope, a fluorescent molecule and an enzyme.

7. The second generation antibody of claim 6, wherein said radioisotope is selected from the group consisting of $^{32}P$, $^{14}C$, $^{3}H$, $^{125}I$ and $^{35}S$.

8. The second generation antibody of claim 6, wherein said fluorescent molecule is selected from the group consisting of fluorescein and rhodamine.

9. The second generation antibody of claim 6, wherein said enzyme is selected from the group consisting of alkaline phosphatase and horseradish peroxidase.

10. The second generation antibody of claim 5, wherein said tumor detecting marker is selected from the group consisting of $^{125}I$, $^{131}I$, $^{123}I$, $^{111}In$, $^{67}Ga$, $^{68}Ga$, $^{99m}Tc$ and Gd.

11. The second generation antibody of claim 5, wherein said therapeutic agent is selected from the group consisting of a radionuclide, drug, toxin and second antibody.

12. The second generation antibody of claim 11, wherein said radionuclide is selected from the group consisting of $^{131}I$, $^{90}Y$, $^{105}Rh$, $^{47}Sc$, $^{67}Cu$, $^{212}Bi$ and $^{211}At$.

13. The second generation antibody of claim 11, wherein said drug is selected from the group consisting of methotrexate and adriamycin.

14. The second generation antibody of claim 11, wherein said second antibody has specific binding affinity to killer T-cells.

15. The monoclonal antibodies of claim 1 that specifically bind the antigen TAG-72 and have a binding affinity in the range of about $3.64 \times 10^9 M^{-1}$ to about $27.72 \times 10^9 M^{-1}$.

16. A method for detecting a human carcinoma or metastases thereof comprising:
(a) obtaining a sample of body fluid or biopsy from a patient;
(b) contacting the body fluid or biopsy with the second generation monoclonal antibody, immunoreactive fragment or antigen binding recombinant thereof of claim 15;
(c) determining the amount of binding of second generation monoclonal antibody, immunoreactive fragment or antigen binding recombinant thereof to the body fluid or biopsy material; and
(d) comparing the amount of binding in step (c) to a control sample or to a predetermined base level; a binding greater than the base level being indicative of the presence of carcinomas or metastases thereof.

17. The method of claim 16, wherein said body fluid is selected from the group consisting of blood, plasma, serum, nipple discharge, cyst fluid, ascites fluids, pleural effusions, seminal plasma, semen, urine and prostatic fluid.

18. The method of claim 16, wherein the amount of monoclonal antibody binding to material present in the body fluid or biopsy is determined by means of a radioimmunoassay.

19. The method of claim 16, wherein the amount of monoclonal antibody binding to substances present in the body fluid or biopsy is determined by means of an enzyme immunoassay.

20. The method of claim 16, wherein said antibody exhibits 0–30% competition with B72.3 antibody.

21. The method of claim 16, wherein said antibody is of an isotype selected from the group consisting of $IgG_{2a}$, $IgG_{2b}$, $IgG_3$ and IgM.

22. A method for localizing carcinoma or metastases thereof comprising:

(a) administering to a patient a second generation monoclonal antibody, immunoreactive fragment or antigen binding recombinant thereof of claim 15, conjugated to an imaging or detecting marker; and (b) exposing the patient to means for detecting said tumor detecting marker, an area of localization of the tumor detecting marker being indicative of the site of the carcinoma or metastasis in said patient.

23. The method of claim 22, wherein said tumor detecting marker is selected from the group consisting of $^{125}I$, $^{131}I$, $^{123}I$, $^{111}In$, $^{113}In$, $^{67}Ga$, $^{68}Ga$, $^{99m}Tc$ and Gd.

24. The method of claim 22, wherein said antibody exhibits 50% more efficiency than B72.3 in targeting human carcinoma in-situ.

25. The method of claim 22, wherein said antibody exhibits 0–30% competition with B72.3 antibody.

26. The method of claim 22, wherein said antibody is of an isotype selected from the group consisting of $IgG_{2a}$, $IgG_{2b}$, $IgG_3$ and IgM.

27. A method for treating a human carcinoma or metastases thereof, comprising administering to a patient afflicted with carcinoma or metastases thereof, an effective amount of a second generation monoclonal antibody, immunoreactive fragment or antigen binding recombinant thereof of claim 15 to inhibit growth and proliferation of said carcinoma or metastasis thereof.

28. The method of claim 27, wherein said antibody is conjugated to a therapeutic agent.

29. The method as claimed in claim 28, wherein said therapeutic agent is selected from the group consisting of a radionuclide, a drug, a toxin, a biological response modifier, and a second antibody.

30. The method of claim 29, wherein said radionuclide is selected from the group consisting of $^{131}I$, $^{90}Y$, $^{105}Rh$, $^{47}Sc$, $^{67}Cu$, $^{212}Bi$ and $^{211}At$.

31. The method of claim 29, wherein said drug is selected from the group consisting of methotrexate and adriamycin.

32. The method of claim 29, wherein said second antibody has specific binding affinity to killer T-cells.

33. The method of claim 27, wherein said antibody exhibits 50% or more efficiency than B72.3 in targeting human carcinoma in-situ.

34. The method of claim 27, wherein said antibody exhibits 0–30% competition with B72.3 antibody.

35. The method as claimed in claim 27, wherein said antibody is of an isotype selected from the group consisting of $IgG_{2a}$, $IgG_{2b}$, $IgG_3$ and IgM.

36. A pharmaceutical composition comprising the monoclonal antibody, immunoreactive fragment or antigen binding recombinant thereof, of claim 15 in an amount sufficient to bind antigens which said monoclonal antibody specifically binds, and a pharmaceutically acceptable, nontoxic, sterile carrier.

37. The monoclonal antibodies of claim 15 produced by a process comprising utilizing affinity chromatography purified TAG-72.

38. The monoclonal antibodies of claim 37 wherein monoclonal antibody B72.3 is employed in affinity chromatography.

39. The method according to claim 27 for treating a human carcinoma or metastases thereof, wherein the carcinoma is a primary colon carcinoma.

40. A composition of matter comprising an immunogenic amount of the monoclonal antibody of claim 1 in a pharmaceutically acceptable carrier.

41. A hybridoma producing a second generation monoclonal antibody which specifically binds both TAG-72 and LS174T antigens but which does not substantially bind normal adult human tissues, wherein said monoclonal antibody has a binding affinity of greater than $3 \times 10^9$ $M^{-1}$ for TAG-72, and wherein said monoclonal antibody is CC49 (ATCC CRL 9459) or CC83 (ATCC CRL 9453) or specifically binds to an epitope specifically bound by CC49 or CC83.

42. A second generation monoclonal antibody, an immunoreactive fragment or an antigen binding recombinant thereof, which specifically binds both TAG-72 and LS174T cell line antigen but which does not substantially bind normal adult human tissues, wherein said monoclonal antibody has a binding affinity of greater than $3 \times 10^9 M^{-1}$ for TAG-72, wherein said monoclonal antibody is CC 46 (ATCC CRL 9458), CC 92 (ATCC CRL 9454), CC 30 (ATCC CRL 9457), CC 11 (ATCC CRL 9455), CC 15 (ATCC CRL 9460), or MATAG 12 (ATCC CRL 9456), or specifically binds to an epitope specifically bound by CC 46, CC 92, CC 30, CC 11, CC 15, or MATAG 12.

43. A method for detecting a human carcinoma or metastases thereof comprising:

(a) obtaining a sample of body fluid or biopsy material from a patient;

(b) contacting the body fluid or biopsy material with the monoclonal antibody of claim 42;

(c) determining the amount of binding of the monoclonal antibody to the body fluid or biopsy material; and (d) comparing the amount of binding in step (c) to a control sample or to a predetermined base level, wherein a binding greater than the base level is indicative of the presence of carcinoma or metastases thereof.

44. A hybridoma producing a second generation monoclonal antibody which specifically binds both TAG-72 and LS174T antigens but which does not substantially bind normal adult human tissues, wherein said monoclonal antibody has a banding affinity of greater than $3 \times 10^9 M^{-1}$ for TAG-79, and wherein said monoclonal antibody is CC 46 (ATCC CRL 9458), CC 92 (ATCC CRL 9454), CC 30 (ATCC CRL 9457), CC 11 (ATCC CRL 9455), CC 15 (ATCC CRL 9460), or MATAG 12 (ATCC CRL 9456), or specifically binds to an epitope specifically bound by CC 46, CC 92, CC 30, CC 11, CC 15 or MATAG 12.

* * * * *